(12) United States Patent
Yoshiara et al.

(10) Patent No.: US 11,801,031 B2
(45) Date of Patent: Oct. 31, 2023

(54) ULTRASOUND DIAGNOSIS APPARATUS

(71) Applicant: CANON MEDICAL SYSTEMS CORPORATION, Otawara (JP)

(72) Inventors: Hiroki Yoshiara, Kawasaki (JP); Tomohisa Imamura, Kawasaki (JP); Koichiro Kurita, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 309 days.

(21) Appl. No.: 16/419,781

(22) Filed: May 22, 2019

(65) Prior Publication Data
US 2019/0357874 A1 Nov. 28, 2019

(30) Foreign Application Priority Data
May 22, 2018 (JP) .................................. 2018-098292

(51) Int. Cl.
A61B 8/08 (2006.01)
A61B 8/06 (2006.01)

(52) U.S. Cl.
CPC ............... *A61B 8/06* (2013.01); *A61B 8/481* (2013.01); *A61B 8/488* (2013.01); *A61B 8/5223* (2013.01); *A61B 8/5246* (2013.01)

(58) Field of Classification Search
CPC ......... A61B 8/06; A61B 8/481; A61B 8/5246; A61B 8/5223; A61B 8/488
See application file for complete search history.

(56) References Cited

U.S. PATENT DOCUMENTS

| 5,220,923 | A | 6/1993 | Hagiwara et al. |
| 6,632,177 | B1 * | 10/2003 | Phillips ................. A61B 8/481 600/458 |
| 2008/0262354 | A1 | 10/2008 | Yoshida et al. |
| 2010/0081938 | A1 * | 4/2010 | Kato ...................... A61B 8/481 600/458 |

(Continued)

FOREIGN PATENT DOCUMENTS

| CN | 103826541 A | 5/2014 |
| CN | 104936531 A | 9/2015 |

(Continued)

OTHER PUBLICATIONS

Combined Chinese Office Action and Search Report dated Nov. 24, 2021 in Patent Application No. 201910428514.X (with English translation of Category of Cited Documents), 9 pages.

(Continued)

*Primary Examiner* — Boniface Ngathi
(74) *Attorney, Agent, or Firm* — Oblon, McClelland, Maier & Neustadt, L.L.P.

(57) ABSTRACT

An ultrasound diagnosis apparatus includes: a transmission and reception circuitry configured to perform, via an ultrasound probe, a first ultrasound scan on a first region in a subject who has a contrast agent injected and a second ultrasound scan on at least a part of a second region in the subject overlapping with the first region, the second ultrasound scan including transmitting and receiving two types of ultrasound waves of which one or both of amplitude levels and phases are different from each other; and processing circuitry configured to generate a blood flow image corresponding to one frame by implementing a Doppler method on the basis of a data sequence including reception data obtained from the first ultrasound scan performed multiple times in mutually the same position within the first region to have the second ultrasound scan performed in-between and to generate a contrast-enhanced image based on a result of the second ultrasound scan performed at least one time.

28 Claims, 20 Drawing Sheets

(56) References Cited

U.S. PATENT DOCUMENTS

| | | | |
|---|---|---|---|
| 2014/0039317 A1* | 2/2014 | Sato | A61B 8/5246 600/443 |
| 2014/0219539 A1* | 8/2014 | Yoshikawa | A61B 5/055 382/134 |
| 2015/0018677 A1* | 1/2015 | Yoshiara | A61B 8/5207 600/431 |
| 2015/0087985 A1 | 3/2015 | Yoshiara et al. | |
| 2015/0094569 A1* | 4/2015 | Ohuchi | A61B 5/5207 600/424 |
| 2015/0257739 A1* | 9/2015 | Yao | A61B 8/481 600/431 |
| 2015/0320395 A1 | 11/2015 | Sato | |
| 2017/0071567 A1* | 3/2017 | Shibata | A61B 8/06 |

FOREIGN PATENT DOCUMENTS

| | | |
|---|---|---|
| JP | 4-99564 A | 3/1992 |
| JP | 2003-299653 | 10/2003 |
| JP | 2006-75426 | 3/2006 |
| JP | 2007-330764 | 12/2007 |
| JP | 2009-119134 | 6/2009 |
| JP | 2010-259672 | 11/2010 |
| JP | 2013-252182 | 12/2013 |
| JP | 2015-97634 A | 5/2015 |
| JP | 2018-15155 | 2/2018 |
| WO | WO 2014/115782 A1 | 7/2014 |

OTHER PUBLICATIONS

Office Action dated Jul. 12, 2022, in corresponding Chinese Patent Application No. 201910428514.X, 17 pages.

Office Action dated Jan. 31, 2023, in corresponding Chinese Patent Application No. 201910428514.X, 7 pages.

Japanese Office Action dated Jan. 10, 2023 in Japanese Patent Application No. 2019-096224, 4 pages.

Notification of rejection dated Jul. 5, 2023, in corresponding Chinese Patent Application No. 201910428514.X, 5 pages.

* cited by examiner

ULTRASOUND DIAGNOSIS APPARATUS

CROSS-REFERENCE TO RELATED APPLICATIONS

This application is based upon and claims the benefit of priority from Japanese Patent Application No. 2018-098292, filed on May 22, 2018; the entire contents of which are incorporated herein by reference.

FIELD

Embodiments described herein relate generally to an ultrasound diagnosis apparatus.

BACKGROUND

Conventionally, ultrasound diagnosis apparatuses implement imaging methods in accordance with various purposes. For example, ultrasound diagnosis apparatuses implement a contrast-enhanced echo method called Contrast Harmonic Imaging (CHI). To perform a contrast harmonic imaging process, for example, a contrast agent is injected through a vein to obtain an image for a medical examination of the heart, the liver, or the like. From the contrast harmonic imaging process, for example, a contrast-enhanced image rendering blood vessels in the subject is obtained.

Further, ultrasound diagnosis apparatuses implement, for example, a Doppler method by which a blood flow is rendered in an image by using the Doppler effect. For example, an ultrasound diagnosis apparatus applies a Moving Target Indicator (MTI) filter to a data sequence in the same position, so as to extract a signal derived from a blood flow, while suppressing a signal (a clutter signal) derived from a stationary tissue or a slow-moving tissue. Further, from the blood flow signal, the ultrasound diagnosis apparatus estimates blood flow information such as blood flow velocity, blood flow dispersion, blood flow power, and the like and further generates blood flow image data indicating a blood flow image (a color Doppler image) in which a distribution of estimated results is, for example, two-dimensionally displayed in color.

DETAILED DESCRIPTION

An ultrasound diagnosis apparatus according to an embodiment includes transmission and reception circuitry and processing circuitry. The transmission and reception circuitry is configured to perform, via an ultrasound probe, a first ultrasound scan on a first region in a subject who has a contrast agent injected and a second ultrasound scan on at least a part of a second region in the subject overlapping with the first region, the second ultrasound scan including transmitting and receiving two types of ultrasound waves of which one or both of amplitude levels and phases are different from each other. The processing circuitry is configured to generate a blood flow image corresponding to one frame by implementing a Doppler method on a basis of a data sequence including pieces of reception data obtained from the first ultrasound scan performed multiple times in a mutually same position within the first region so as to have the second ultrasound scan performed in-between and to generate a contrast-enhanced image based on a result of the second ultrasound scan performed at least one time.

Exemplary embodiments of an ultrasound diagnosis apparatus will be explained below, with reference to the accompanying drawings. The explanation of each of the embodiments and the modification examples may similarly be applied to any other embodiment or modification example.

First Embodiment

Figure 1:
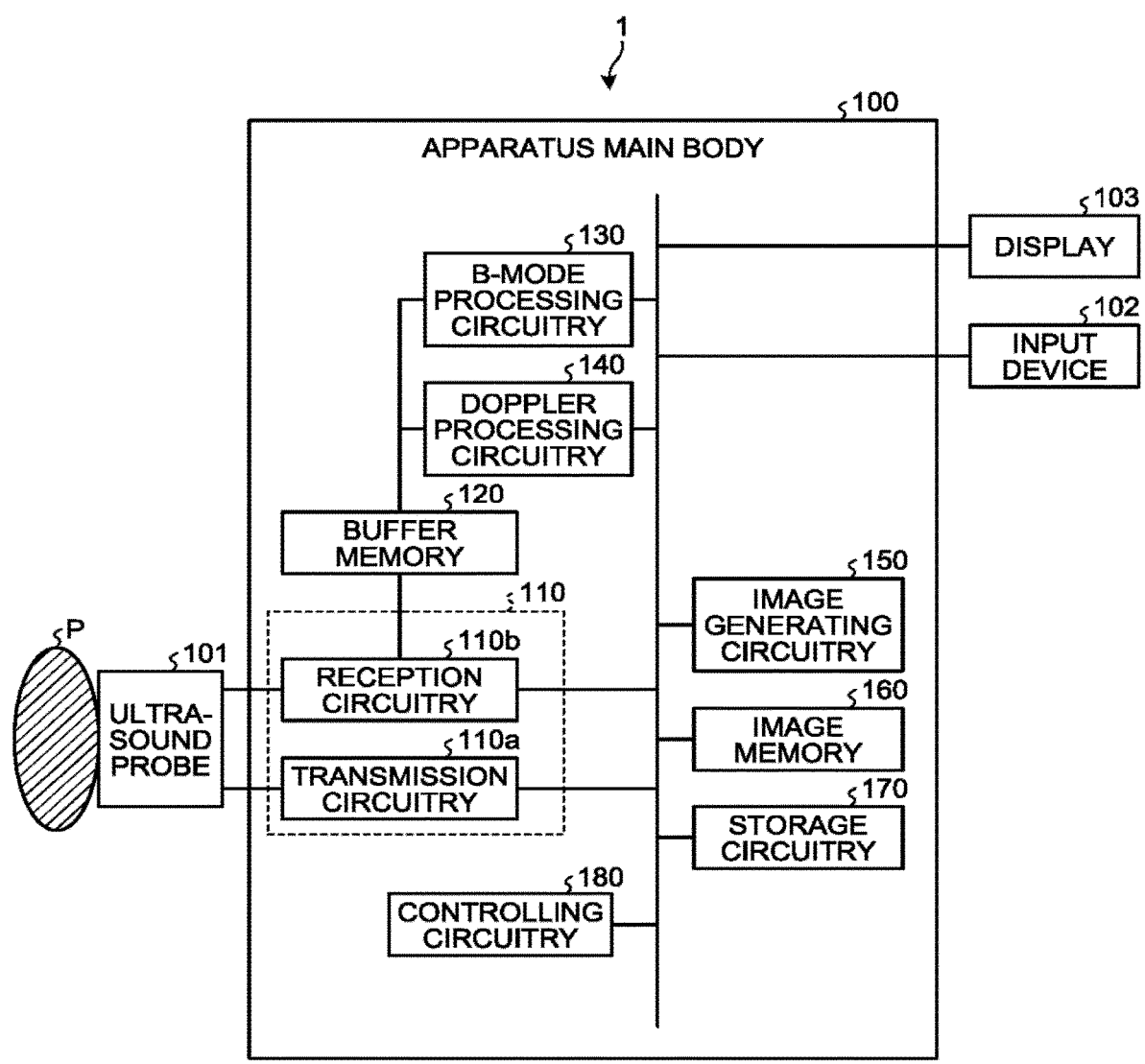
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input device 102, and a display 103.

The ultrasound probe 101 includes, for example, a plurality of elements such as piezoelectric transducer elements. Each of the plurality of elements is configured to generate an ultrasound wave on the basis of a drive signal supplied thereto from transmission circuitry 110a in transmission and reception circuitry 110 included in the apparatus main body 100. Further, the ultrasound probe 101 is configured to receive reflected waves from an examined subject (hereinafter "subject") P and to convert the received reflected waves into electrical signals. Further, for example, the ultrasound probe 101 includes a matching layer provided for the piezoelectric transducer elements, as well as a backing member or the like that prevents the ultrasound waves from propagating rearward from the piezoelectric transducer elements. The ultrasound probe 101 is detachably connected to the apparatus main body 100.

When an ultrasound wave is transmitted from the ultrasound probe 101 to the subject P, the transmitted ultrasound wave is repeatedly reflected on a surface of discontinuity of acoustic impedances at a tissue in the body of the subject P and is received as a reflected-wave signal by each of the plurality of elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction. Further, the ultrasound probe 101 outputs the reflected-wave signals to reception circuitry 110b included in the transmission and reception circuitry 110.

The ultrasound probe 101 is provided so as to be attachable to and detachable from the apparatus main body 100. When a two-dimensional region in the subject P is to be scanned (a two-dimensional scan), an operator connects, for example, a one-dimensional (1D) array probe in which the plurality of piezoelectric transducer elements are arranged in a row to the apparatus main body 100, as the ultrasound probe 101. The 1D array probe may be a linear-type ultrasound probe, a convex-type ultrasound probe, a sector-type ultrasound probe, or the like. In contrast, when a three-dimensional region in the subject P is to be scanned (a three-dimensional scan), the operator connects, for example, a mechanical four-dimensional (4D) probe or a two-dimensional (2D) array probe to the apparatus main body 100, as the ultrasound probe 101. The mechanical 4D probe is capable of performing a two-dimensional scan by using the plurality of piezoelectric transducer elements arranged in a row such as those in the 1D array probe and is also capable of performing a three-dimensional scan by swinging the plurality of piezoelectric transducer elements at a predetermined angle (a swinging angle). Further, the 2D array probe is capable of performing a three-dimensional scan by using the plurality of piezoelectric transducer elements arranged in a matrix formation and is also capable of performing a two-dimensional scan by transmitting ultrasound waves in a converged manner.

The input device 102 is realized, for example, with input means such as a mouse, a keyboard, a button, a panel switch, a touch command screen, a foot switch, a trackball, a joystick, and/or the like. The input device 102 is configured to receive various types of setting requests from the operator of the ultrasound diagnosis apparatus 1 and to transfer the received various types of setting requests to the apparatus main body 100.

For example, the display 103 is configured to display a Graphical User Interface (GUI) used by the operator of the ultrasound diagnosis apparatus 1 for inputting the various types of setting requests through the input device 102 and to display an ultrasound image represented by ultrasound image data generated by the apparatus main body 100 and the like. The display 103 is realized by using a liquid crystal monitor, a Cathode Ray Tube (CRT) monitor, or the like.

The apparatus main body 100 is configured to generate the ultrasound image data on the basis of the reflected-wave signals received by the ultrasound probe 101. The ultrasound image data is an example of image data. The apparatus main body 100 is capable of generating two-dimensional ultrasound image data on the basis of reflected-wave data corresponding to a two-dimensional region of the subject P received by the ultrasound probe 101. Further, the apparatus main body 100 is also capable of generating three-dimensional ultrasound image data on the basis of reflected-wave data corresponding to a three-dimensional region of the subject P received by the ultrasound probe 101. As illustrated in FIG. 1, the apparatus main body 100 includes the transmission and reception circuitry 110, a buffer memory 120, B-mode processing circuitry 130, Doppler processing circuitry 140, image generating circuitry 150, an image memory 160, storage circuitry 170, and controlling circuitry 180.

Under control of the controlling circuitry 180, the transmission and reception circuitry 110 is configured to cause ultrasound waves to be transmitted from the ultrasound probe 101 and to cause the ultrasound waves (the reflected-waves of the ultrasound waves) to be received by the ultrasound probe 101. In other words, the transmission and reception circuitry 110 performs an ultrasound scan (scanning with the ultrasound waves) via the ultrasound probe 101. The transmission and reception circuitry 110 is an example of a transmitting and receiving unit. The transmission and reception circuitry 110 includes the transmission circuitry 110a and the reception circuitry 110b.

Under the control of the controlling circuitry 180, the transmission circuitry 110a causes the ultrasound waves to be transmitted from the ultrasound probe 101. The transmission circuitry 110a includes rate pulser generating circuitry, transmission delay circuitry, and a transmission pulser, and is configured to supply the drive signal to the ultrasound probe 101. When scanning a two-dimensional region in the subject P, the transmission circuitry 110a causes an ultrasound beam used for scanning the two-dimensional region to be transmitted from the ultrasound probe 101. Further, when scanning a three-dimensional region in the subject P, the transmission circuitry 110a causes an ultrasound beam used for scanning the three-dimensional region to be transmitted from the ultrasound probe 101.

The rate pulser generating circuitry is configured to repeatedly generate a rate pulse used for forming a transmission ultrasound wave (a transmission beam) at a predetermined rate frequency (a Pulse Repetition Frequency [PRF]). Voltage is applied to the transmission pulser, while the rate pulses have mutually-different transmission delay periods as a result of being routed through the transmission delay circuitry. For example, the transmission delay circuitry is configured to apply a transmission delay period that is required to converge the ultrasound waves generated by the ultrasound probe 101 into the form of a beam and to determine transmission directionality and that corresponds to each of the piezoelectric transducer elements, to each of the rate pulses generated by the rate pulser generating circuitry. The transmission pulser is configured to apply the drive signal (a drive pulse) to the ultrasound probe 101 with timing based on the rate pulses. In this situation, by varying the transmission delay periods applied to the rate pulses, the transmission delay circuitry arbitrarily adjusts the transmission directions of the ultrasound waves transmitted from the surfaces of the piezoelectric transducer elements.

After being transferred from the transmission pulser to the piezoelectric transducer elements in the ultrasound probe 101 via a cable, the drive pulse is converted from electric signals to mechanical vibration in the piezoelectric transducer elements. The ultrasound waves generated by the mechanical vibration are transmitted to the inside of the subject's body. In this situation, the ultrasound waves having the mutually-different transmission delay periods in correspondence with the piezoelectric transducer elements are converged and propagated into a predetermined direction.

The transmission circuitry 110a has a function that is able to instantly change the transmission frequency, the transmission drive voltage, and the like, for the purpose of executing a predetermined scan sequence under the control of the controlling circuitry 180. In particular, the function to change the transmission drive voltage is realized by using linear-amplifier-type transmission circuitry of which the value can be instantly switched or by using a mechanism configured to electrically switch between a plurality of power source units.

The reflected waves of the ultrasound waves transmitted by the ultrasound probe 101 reach the piezoelectric transducer elements provided in the ultrasound probe 101 and are subsequently converted from the mechanical vibration into electrical signals (the reflected-wave signals) in the piezoelectric transducer elements and are input to the reception circuitry 110b. The reception circuitry 110b includes a pre-amplifier, an Analog-to-Digital (A/D) converter, quadrature detecting circuitry, and the like and is configured to generate reflected-wave data by performing various types of processes on the reflected-wave signals received by the ultrasound probe 101. Further, the reception circuitry 110b is configured to store the generated reflected-wave data into the buffer memory 120.

The pre-amplifier is configured to amplify the reflected-wave signal for each of the channels and to perform a gain adjustment process (a gain correcting process). The A/D converter is configured to convert the gain-corrected reflected-wave signals into digital signals, by performing an A/D conversion on the gain-corrected reflected-wave signals. The quadrature detecting circuitry is configured to convert the reflected-wave signals resulting from the A/D conversion into an In-phase signal (an I signal) and a Quadrature-phase signal (a Q signal) that are in a baseband. Further, the quadrature detecting circuitry is configured to store the I signal and the Q signal (the IQ signals) into the buffer memory 120 as the reflected-wave data.

The reception circuitry 110b is configured to generate two-dimensional reflected-wave data from two-dimensional reflected-wave signals received by the ultrasound probe 101. Further, the reception circuitry 110b is configured to generate three-dimensional reflected-wave data from three-dimensional reflected-wave signals received by the ultrasound probe 101.

In this situation, the ultrasound diagnosis apparatus 1 according to the present embodiment is configured to simultaneously display a blood flow image indicating blood flow information, a contrast-enhanced image rendering a tissue perfusion of small capillaries or the like, and a tissue image indicating a tissue shape. The blood flow image is an image represented by color Doppler image data serving as blood flow image data. The contrast-enhanced image is an image represented by B-mode image data serving as contrast-enhanced image data. The tissue image is an image represented by B-mode image data serving as tissue image data.

Further, to realize the display, the transmission and reception circuitry 110 is configured to perform an ultrasound scan (a first ultrasound scan) to acquire the blood flow image data in a Doppler mode and to perform an ultrasound scan (a second ultrasound scan) to acquire the tissue image data and the contrast-enhanced image data in a B-mode. The first ultrasound scan is an ultrasound scan performed on a region (a first region) in the subject P who has a contrast agent injected and is an ultrasound scan performed to obtain blood flow information in the first region. The second ultrasound scan is an ultrasound scan performed to obtain information about the tissue shape in a region (a second region) inside the subject P and information about the tissue perfusion of small capillaries or the like.

In other words, to acquire the tissue image data and the contrast-enhanced image data, the transmission and reception circuitry 110 performs the single type of scans called the second ultrasound scans, instead of separately performing an ultrasound scan to acquire a tissue image and another ultrasound scan to acquire a contrast-enhanced image. In other words, as a result of the transmission and reception circuitry 110 simply performing the two types of ultrasound scans, namely the first ultrasound scans and the second ultrasound scans, the ultrasound diagnosis apparatus 1 is able to acquire the three types of images, namely, the blood flow image, the tissue image, and the contrast-enhanced image.

It is sufficient when the first region and the second region at least partially overlap with each other. The area of the first region and the area of the second region may be the same. The area of the first region may be smaller than the area of the second region. Conversely, the area of the second region may be smaller than the area of the first region.

The buffer memory 120 is a memory configured to temporarily store therein the reflected-wave data generated by the transmission and reception circuitry 110. For example, the buffer memory 120 stores therein reflected-wave data corresponding to a number of frames or reflected-wave data corresponding to a number of volumes. For example, the buffer memory 120 stores therein reflected-wave data corresponding to a prescribed number of frames, under control of the reception circuitry 110b. Further, when reflected-wave data corresponding to one frame is newly generated by the reception circuitry 110b while the buffer memory 120 is in the state of storing therein the reflected-wave data corresponding to the prescribed number of frames, the buffer memory 120 discards the reflected-wave data corresponding to the one frame that was generated earliest and stores therein the newly-generated reflected-wave data corresponding to the one frame, under the control of the reception circuitry 110b. For example, the buffer memory 120 is realized by using a semiconductor memory element such as a Random Access Memory (RAM), a flash memory, or the like. The reflected-wave data corresponding to one frame and being generated by the transmission and reception circuitry 110 is reflected-wave data corresponding to one acquired frame.

The B-mode processing circuitry 130 and the Doppler processing circuitry 140 are signal processing units configured to read any of the reflected-wave data from the buffer memory 120 and to perform various types of signal processing processes on the read reflected-wave data.

The B-mode processing circuitry 130 is configured to generate data (B-mode data) in which the signal intensity (amplitude intensity) corresponding to each sampling point is expressed by a degree of brightness, by performing a logarithmic amplification and an envelope detecting process or the like on the reflected-wave data read from the buffer memory 120. The B-mode processing circuitry 130 is configured to output the generated B-mode data to the image generating circuitry 150. The B-mode processing circuitry 130 is realized by using a processor, for example.

The B-mode processing circuitry 130 is capable of changing the frequency band to be rendered in a picture, by varying the detected frequency. By using this function of the B-mode processing circuitry 130, the ultrasound diagnosis apparatus 1 according to the first embodiment is capable of implementing Contrast Harmonic Imaging (CHI) by which a non-linear signal from the contrast agent is rendered in a picture. For example, the B-mode processing circuitry 130 is capable of generating B-mode data (second B-mode data) from which the contrast-enhanced image data is generated. Specific processes performed by the B-mode processing circuitry 130 according to the first embodiment will be explained in detail later.

By performing a frequency analysis on the reflect-wave data read from the buffer memory 120, the Doppler processing circuitry 140 is configured to extract motion information of moving members (a blood flow, a tissue, a contrast agent echo component, and the like) based on the Doppler effect and to generate data (Doppler data) indicating the extracted motion information. For example, as the motion information of the moving members, the Doppler processing circuitry 140 extracts an average velocity value, an average dispersion value, an average power value, and the like from multiple points and generates the Doppler data indicating the extracted motion information of the moving members. The Doppler processing circuitry 140 is configured to output the generated Doppler data to the image generating circuitry 150.

By using the function of the Doppler processing circuitry 140 described above, the ultrasound diagnosis apparatus 1 according to the first embodiment is capable of implementing a color Doppler method that may be called a Color Flow Mapping (CFM) method. According to the color flow mapping method, ultrasound waves are transmitted and received multiple times on a plurality of scanning lines. Further, according to the color flow mapping method, by applying a Moving Target Indicator (MTI) filter to a data sequence in the same position, a signal derived from a blood flow is extracted from the data sequence in the same position, while suppressing a signal (clutter signal) derived from a stationary tissue or a slow-moving tissue. Further, according to the color flow mapping method, blood flow information such as velocity of the blood flow, dispersion of the blood flow, and power of the blood flow are estimated from the blood flow signal. The image generating circuitry 150 (explained later) is configured to generate ultrasound image data (blood flow image data: color Doppler image data) in which a distribution of estimated results of the blood flow information is two-dimensionally displayed in color. Further, the display 103 is configured to display a blood flow image represented by the blood flow image data.

As the MTI filter, the Doppler processing circuitry 140 according to the present embodiment uses an adaptive MTI filter configured to vary a coefficient in accordance with an input signal. For example, as the adaptive MTI filter, the Doppler processing circuitry 140 uses a filter called "Eigenvector Regression Filter". In the following sections, such an "Eigenvector Regression Filter" serving as an adaptive MTI filter that uses eigenvectors will be referred to as an "eigenvector MTI filter".

The eigenvector MTI filter is configured to calculate an eigenvector from a correlation matrix and to calculate a coefficient to be used in the clutter component suppressing process from the calculated eigenvector. This method is an application of a method used in a main component analysis, a Karhunen-Loeve transform, or an eigenspace method.

The Doppler processing circuitry 140 according to the first embodiment that uses the eigenvector MTI filter is configured to calculate a correlation matrix of the first region from the data sequence including consecutive pieces of reflected-wave data in mutually the same position (the same sampling point). Further, the Doppler processing circuitry 140 is configured to calculate eigenvalues of the correlation matrix and eigenvectors corresponding to the eigenvalues. Further, the Doppler processing circuitry 140 is configured to calculate a matrix obtained by reducing the rank of a matrix in which the eigenvectors are arranged on the basis of magnitudes of the eigenvalues, as a filter matrix used for suppressing the clutter component.

Further, by using the filter matrix, the Doppler processing circuitry 140 is configured to specify a data sequence extracting a blood flow signal derived from the blood flow while suppressing the clutter component, from the data sequence including the consecutive pieces of reflected-wave data in mutually the same position (the same sampling point). Further, the Doppler processing circuitry 140 is configured to estimate the blood flow information by performing a calculation such as an autocorrelation calculation by using the specified data sequence. Further, the Doppler processing circuitry 140 is configured to output Doppler data indicating the estimated blood flow information, to the image generating circuitry 150. Specific processes performed by the Doppler processing circuitry 140 according to the first embodiment will be explained in detail later. The Doppler processing circuitry 140 is realized by using, for example, a processor. The Doppler processing circuitry 140 is an example of a blood flow information obtaining unit.

The B-mode processing circuitry 130 and the Doppler processing circuitry 140 are capable of processing both two-dimensional reflected-wave data and three-dimensional reflected-wave data.

The image generating circuitry 150 is configured to generate the ultrasound image data from the data output by the B-mode processing circuitry 130 and the Doppler processing circuitry 140. The image generating circuitry 150 is configured to generate two-dimensional B-mode image data in which intensities of reflected waves are expressed with degrees of brightness, from the two-dimensional B-mode data generated by the B-mode processing circuitry 130. Further, the image generating circuitry 150 is configured to generate two-dimensional Doppler image data in which the blood flow information is rendered in a picture, from the two-dimensional Doppler data generated by the Doppler processing circuitry 140. The two-dimensional Doppler image data is velocity image data, dispersion image data, power image data, or image data combining together any of these types of image data. From the Doppler data serving as the blood flow information, the image generating circuitry 150 is configured to generate, as Doppler image data, blood flow image data in which the blood flow information is displayed in color or blood flow image data in which one piece of blood flow information is displayed in a gray scale. The image generating circuitry 150 is realized by using a processor.

In this situation, generally speaking, the image generating circuitry 150 converts (by performing a scan convert process) a scanning line signal sequence from an ultrasound scan into a scanning line signal sequence in a video format used by, for example, television and generates display-purpose ultrasound image data. For example, the image generating circuitry 150 generates the display-purpose ultrasound image data by performing a coordinate transformation process compliant with the ultrasound scanning mode used by the ultrasound probe 101. Further, as various types of image processing processes besides the scan convert process, the image generating circuitry 150 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuitry 150 combines text information of various types of parameters, scale graduations, body marks, and the like with the ultrasound image data.

Further, the image generating circuitry 150 generates three-dimensional B-mode image data by performing a coordinate transformation process on the three-dimensional B-mode data generated by the B-mode processing circuitry 130. Further, the image generating circuitry 150 generates three-dimensional Doppler image data by performing a coordinate transformation process on the three-dimensional Doppler Data generated by the Doppler processing circuitry 140. In other words, the image generating circuitry 150 is configured to generate the "three dimensional B-mode image data and three-dimensional Doppler image data" as "three-dimensional ultrasound image data (volume data)". Further, the image generating circuitry 150 is configured to perform various rendering processes on the volume data to generate various types of two-dimensional image data used for displaying the volume data on the display 103.

Examples of the rendering process performed by the image generating circuitry 150 include a process of generating MPR image data from the volume data by implementing a Multi Planar Reconstruction (MPR) method, for example. Another example of the rendering process performed by the image generating circuitry 150 is a Volume Rendering (VR) process by which two-dimensional image data reflecting three-dimensional information is generated. The image generating circuitry 150 is an example of an image generating unit.

The B-mode data and the Doppler data are each ultrasound image data before the scan convert process. The data generated by the image generating circuitry 150 is the display-purpose ultrasound image data after the scan convert process. The B-mode data and the Doppler data may be referred to as raw data.

The image memory 160 is a memory configured to store therein various types of image data generated by the image generating circuitry 150. Further, the image memory 160 is also configured to store therein any of the data generated by the B-mode processing circuitry 130 and the Doppler processing circuitry 140. After a diagnosis process, for example, the operator is able to refer to any of the B-mode data and the Doppler data stored in the image memory 160. The B-mode data and Doppler data that are referred to can serve as display-purpose ultrasound image data after being routed through the image generating circuitry 150. For example, the image memory 160 is realized by using a semiconductor memory element such as a RAM, a flash memory, or the like, or a hard disk or an optical disk.

The storage circuitry 170 is configured to store therein control programs for performing ultrasound wave transmissions and receptions, image processing processes, and display processes as well as various types of data such as diagnosis information (e.g., subjects' IDs, medical doctors' observations), diagnosis protocols, various types of body marks, and the like. Further, the storage circuitry 170 may also be used, as necessary, for saving therein any of the data stored in the image memory 160, and the like. For example, the storage circuitry 170 is realized by using a semiconductor memory element such as a flash memory, a hard disk, or an optical disk.

The controlling circuitry 180 is configured to control the entirety of processes performed by the ultrasound diagnosis apparatus 1. More specifically, on the basis of the various types of setting requests input from the operator via the input device 102 and the various types of control programs and various types of data read from the storage circuitry 170, the controlling circuitry 180 controls processes performed by the transmission and reception circuitry 110, the B-mode processing circuitry 130, the Doppler processing circuitry 140, and the image generating circuitry 150. Further, the controlling circuitry 180 controls the display 103 so as to display the ultrasound image represented by the display-purpose ultrasound image data stored in the image memory 160. The controlling circuitry 180 is an example of a display controlling unit or a controlling unit. The controlling circuitry 180 may be realized by using a processor, for example. The ultrasound image is an example of images.

Further, by controlling the ultrasound probe 101 via the transmission and reception circuitry 110, the controlling circuitry 180 is configured to control ultrasound scans. For example, the controlling circuitry 180 is configured to control the first ultrasound scans and the second ultrasound scans described above.

The term "processor" used in the above explanations denotes, for example, a Central Processing Unit (CPU), a Graphics Processing Unit (GPU), or a circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in the storage circuitry 170. In this situation, instead of saving the programs in the storage circuitry 170, it is also acceptable to directly incorporate the programs in the circuits of the processors. In that situation, the processors realize the functions thereof by reading and executing the programs incorporated in the circuits thereof. The processors in the present embodiment do not each necessarily have to be structured as a single circuit. It is also acceptable to structure one processor by combining together a plurality of independent circuits so as to realize the functions thereof. Further, it is also acceptable to integrate two or more of the constituent elements in FIG. 1 into one processor so as to realize the functions thereof.

An overall configuration of the ultrasound diagnosis apparatus 1 according to the first embodiment has thus been explained.

In the first embodiment, the transmission and reception circuitry 110 performs, via the ultrasound probe 101, the first ultrasound scans and the second ultrasound scans so as to alternate. Further, as for the scanning mode of the first ultrasound scans, the ultrasound wave is transmitted and received once with respect to each of the scanning lines, in the first region formed with the plurality of scanning lines. By using this scanning mode, it is possible to improve the framerate. In the following sections, the first ultrasound scans will be referred to as "high framerate ultrasound scans". The CFM method implemented by performing the "high framerate ultrasound scans" will be referred to as "high framerate method".

Incidentally, according to an ordinary color Doppler method, ultrasound wave transmission and reception is performed multiple times in the same direction, so as to extract a blood flow signal from the signal received in this manner. The data sequence including reflected-wave signals (reflected-wave data) from mutually the same position obtained from the ultrasound wave transmissions and receptions performed in this manner is called a "packet". A packet size denotes the number of times the ultrasound wave transmission and reception is performed in the same direction to obtain the blood flow information corresponding to one frame. The packet size in a generally-used color Doppler method is approximately in the range of 5 to 16. Levels of performance of eigenvector MTI filters are improved when the packet size is larger. However, when the packet size is increased, the framerate becomes lower.

In contrast, according to the high framerate method, it is possible to perform processes on data sequences in the same position in different frames, in the frame direction (time direction). For example, according to the high framerate method, it is possible to perform the MTI filtering process as a process performed on data of an infinite length, in contrast to the data processing having a finite length of the packet. As a result, by using the high framerate method, it is possible to improve the level of performance of the MTI filter. Consequently, it is possible to also detect blood flow information related to a blood flow having a lower flowrate. It is also possible to display a blood flow image indicating blood flow information at a higher framerate.

Together with the first ultrasound scans realized with the high framerate ultrasound scans, the controlling circuitry 180 according to the first embodiment is also configured to perform the second ultrasound scans in a scanning mode explained below.

The controlling circuitry 180 divides the second region into a plurality of segmented regions and causes the ultrasound probe 101 to perform the second ultrasound scan on each of the plurality of segmented regions in a time-division manner between the first ultrasound scans. In other words, the transmission and reception circuitry 110 is configured to perform, via the ultrasound probe 101, the first ultrasound scans and the second ultrasound scans so as to alternate, the second ultrasound scans being performed on the plurality of segmented regions obtained by dividing the second regions into segments. Accordingly, in the first embodiment, the transmission and reception circuitry 110 performs each of the second ultrasound scans between the first ultrasound scans so as to complete the second ultrasound scans corresponding to one frame, during the time period when the first ultrasound scans corresponding to a number of frames are performed. By using this scanning mode, the ultrasound diagnosis apparatus 1 according to the first embodiment is able to set ultrasound wave transmission and reception conditions (image quality conditions) for the first ultrasound scans and for the second ultrasound scans, independently of each other.

Figure 2:
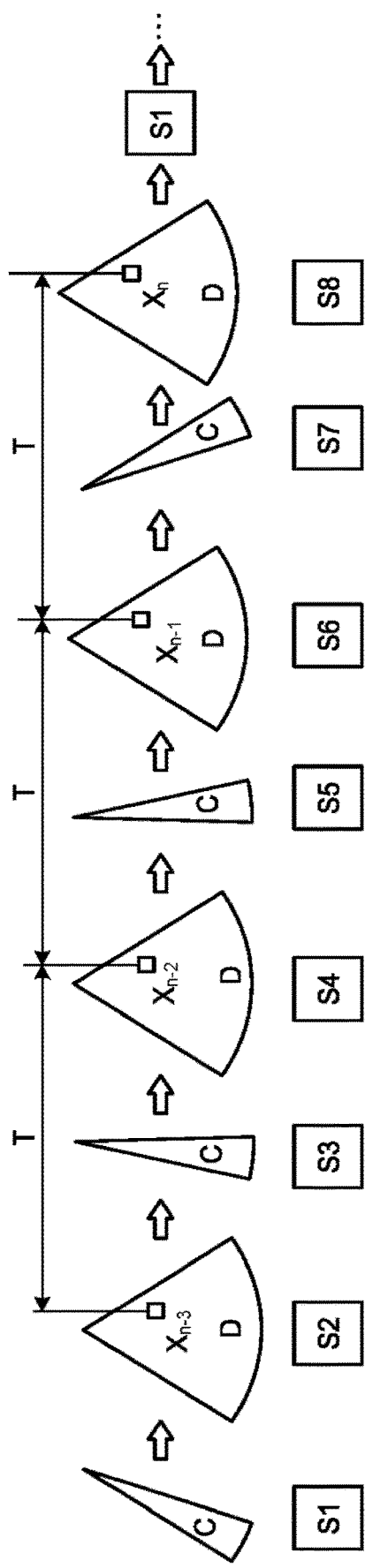
FIG. 2 is a drawing for explaining examples of first ultrasound scans and second ultrasound scans according to the first embodiment.
Figure 3:
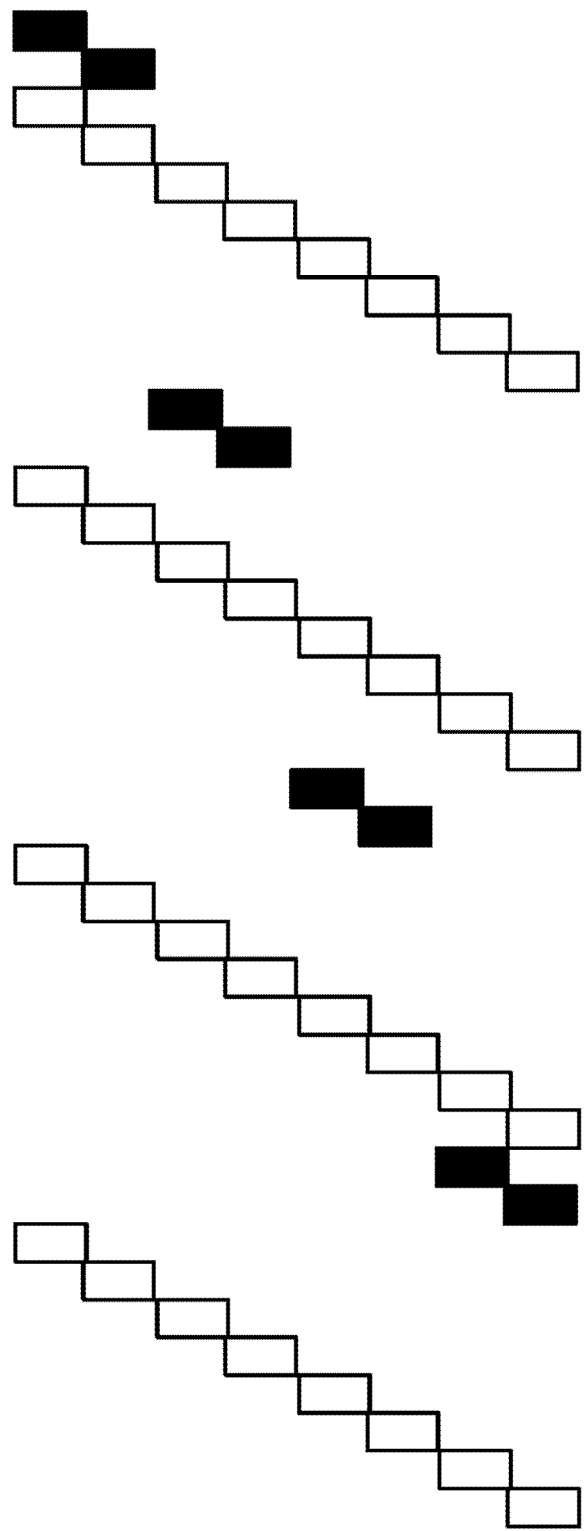
FIG. 3 is another drawing for explaining the examples of the first ultrasound scans and the second ultrasound scans according to the first embodiment.

Next, the first ultrasound scans and the second ultrasound scans will be explained. FIGS. 2 and 3 are drawings for explaining examples of the first ultrasound scans and the second ultrasound scans according to the first embodiment. As illustrated in FIG. 2, on the basis of an instruction from the operator or information in an initial setting or the like, the controlling circuitry 180 divides the second region into four segmented regions (first to fourth segmented regions). In FIG. 2, the letter "C" indicates each of the segmented regions on which the second ultrasound scans are performed by using a transmission and reception condition for a contrast harmonic imaging process in the B-mode. Each of the segmented regions is formed with at least one scanning line.

For example, in the present embodiment, a Phase Modulation (PM) method may be used in the second ultrasound scans. The phase modulation method is a method by which, for example, two types of ultrasound waves having mutually-different phases are transmitted with respect to each of the scanning lines structuring a scanned range, so that pieces of reflected-wave data based on reflected waves of the two types of ultrasound waves are added together. In the present embodiment, when the phase modulation method is used, the transmission and reception circuitry 110 transmits two types of ultrasound waves having mutually-different phases with respect to each of the scanning lines structuring the segmented regions, so that the B-mode processing circuitry 130 adds together the pieces of reflected-wave data based on the reflected waves of the two types of ultrasound waves. When the phase modulation method is used, the second ultrasound scans include transmitting and receiving the two types of ultrasound waves having the mutually-different phases.

Alternatively, in the second ultrasound scans, an Amplitude Modulation (AM) method may be used. The amplitude modulation method is a method by which, for example, three ultrasound waves being modulated to have an amplitude ratio of "1:2:1" while having mutually the same phase are transmitted with respect to each of the scanning lines structuring a scanned range, so that an addition/subtraction process is performed on pieces of reflected-wave data based on reflected waves of the three ultrasound waves. In the present embodiment, when the amplitude modulation method is used, with respect to each of the scanning lines structuring the segmented regions, the transmission and reception circuitry 110 transmits an ultrasound wave of which the amplitude is "0.5", another ultrasound wave of which the amplitude is "1", and yet another ultrasound wave of which the amplitude is "0.5" in the stated order. In other words, the transmission and reception circuitry 110 transmits the two types of ultrasound waves having mutually-different amplitude values. Further, the B-mode processing circuitry 130 performs the addition/subtraction process on the pieces of reflected-wave data based on the reflected waves of the three ultrasound waves (the two types of ultrasound waves). When the amplitude modulation method is used, the second ultrasound scans include transmitting and receiving the two types of ultrasound waves having the mutually-different amplitude values.

The operator selects which modulation method is to be used in the second ultrasound scans, either the phase modulation method or the amplitude modulation method. For example, in the phase modulation method, because the frequency of the transmitted ultrasound waves is relatively high and the reception frequency is relatively high to extract second harmonic component from contrast agent, it is possible to obtain an ultrasound image having a relatively high spatial resolution, but the phase modulation method has a characteristic where the penetration is not excellent. In contrast, in the amplitude modulation method, because the frequency of the transmitted ultrasound waves is relatively low and the reception frequency is almost same as transmitted frequency, the penetration is excellent, but the amplitude modulation method has a characteristic where the spatial resolution of the ultrasound image is relative low. While taking these characteristics into consideration, the operator selects one from between the phase modulation method and the amplitude modulation method, by operating the input device 102.

For example, when the phase modulation method is selected by the operator, the controlling circuitry 180 stores information "0" indicating the phase modulation method into a predetermined region within the entire storage region of the storage circuitry 170. Further, when the amplitude modulation method is selected by the operator, the controlling circuitry 180 stores information "1" indicating the amplitude modulation method into the predetermined region of the storage circuitry 170. After that, when executing the second ultrasound scans, the controlling circuitry 180 references the predetermined region of the storage circuitry 170. When the information obtained from the referencing indicates "0", the controlling circuitry 180 controls the transmission and reception circuitry 110 and the B-mode processing circuitry 130 so that the processes using the phase modulation method described above are performed. On the contrary, when the information obtained from the referencing indicates "1", the controlling circuitry 180 controls the transmission and reception circuitry 110 and the B-mode processing circuitry 130 so that the processes using the amplitude modulation method described above are performed.

Further, in FIG. 2, the letter "D" denotes the first region on which the first ultrasound scans are performed by using a transmission and reception condition for the color Doppler mode. For example, the letter "D" in FIG. 2 denotes a range in which an ultrasound scan is performed by implementing the high framerate method described above. In other words, in the first ultrasound scans, the ultrasound wave is transmitted and received once with respect to each of the scanning lines, unlike the generally-used color Doppler method by which an ultrasound wave is transmitted multiple times in the same direction to receive reflected-waves multiple times. As the first ultrasound scans, the transmission and reception circuitry 110 transmits and receives the ultrasound wave once with respect to each of the plurality of scanning lines forming the first region. In this manner, the ultrasound scan is performed on the basis of the method (the high framerate method) by which the blood flow information is obtained by using the reflected waves corresponding to the plurality of frames (the plurality of acquired frames).

As illustrated in FIG. 2, the transmission and reception circuitry 110 at first performs the second ultrasound scans on the first segmented region (step S1) and performs the first ultrasound scans on the first region (corresponding to one frame) (step S2). Further, the transmission and reception circuitry 110 performs the second ultrasound scans on the second segmented region (step S3) and performs the first ultrasound scans on the first region (step S4). After that, the transmission and reception circuitry 110 performs the second ultrasound scans on the third segmented region (step S5) and performs the first ultrasound scans on the first region (step S6). Subsequently, the transmission and reception circuitry 110 performs the second ultrasound scans on the fourth segmented region (step S7), performs the first ultrasound scans on the first region (step SB), and returns to step S1.

In this situation, as illustrated in FIG. 2, the controlling circuitry 180 controlling the first ultrasound scans performed by the transmission and reception circuitry 110 arranges the intervals at which the first ultrasound scans are performed to be regular intervals. In other words, a "point X" on a "certain scanning line" in the first region is scanned once in each of the first ultrasound scans performed at steps S2, S4, S6, and S8 in FIG. 2, while the scanning intervals thereof is controlled to be constant as "T". For example, the controlling circuitry 180 arranges the intervals at which the first ultrasound scans are performed to be regular intervals, by keeping the time periods required by the second ultrasound scans to be the same as one another. For example, the controlling circuitry 180 exercises control so that the time periods required by the second ultrasound scans performed at steps S1, S3, S5, and S7 in FIG. 2 to be the same length of time. The controlling circuitry 180 arranges the sizes of the segmented regions obtained by dividing the second region, the number of scanning lines, the density and the depth of the scanning lines, and the like to be the same as one another. For example, when the numbers of scanning lines are the same, the time periods required by the second ultrasound scans will be the same as one another. The Doppler processing circuitry 140 is configured to output blood flow information of the "point X" by performing the process described below on a data sequence ("$X_{n-3}$, $X_{n-2}$, $X_{n-1}$, $X_n$, . . . " illustrated in FIG. 2) in the same position within the first region among the frames. In the method described above, the controlling circuitry 180 having a display controlling function updates one part of the tissue image corresponding to a segmented region at the intervals "T", instead of updating the tissue image displayed on the display 103 at the intervals of "4T".

In a conventional color Doppler process, the "MTI filtering process" and the "process of estimating velocity, dispersion, and power" are performed on a data sequence closed within the packet. For this reason, in the conventional color Doppler process, it is possible to output only one piece of blood flow information with respect to one packet. In contrast, in the color Doppler process performed in the scanning mode implementing the high framerate method, there is no concept of packets in the scans themselves. Accordingly, in the color Doppler process performed in the scanning mode described above, it is possible to arbitrarily change the data length of the data sequence used in the process performed for outputting one piece of blood flow information.

Further, in the color Doppler process performed in the scanning mode described above, it is possible to arrange a data sequence used in the process performed for outputting blood flow information in a former temporal phase to overlap with a data sequence used in the process performed for outputting blood flow information in a latter temporal phase.

This aspect will be explained with reference to FIG. 3. FIG. 3 illustrates an example in which the first region and the second region represent mutually the same scanned range, while the scanned range is formed with eight scanning lines, namely, first to eighth scanning lines. Further, in FIG. 3, the eight scanning lines are numbered as "1, 2, 3, 4, 5, 6, 7, and 8" along the azimuth direction (the direction in which the transducer elements are arranged in the ultrasound probe 101). Further, in FIG. 3, the second ultrasound scans are indicated with black rectangles, while the first ultrasound scans are indicated with white rectangles. FIG. 3 is a drawing illustrating the example in which the scanned range illustrated in FIG. 2 is scanned in the scanning mode according to the first embodiment. More specifically, FIG. 3 illustrates the example in which the first region illustrated in FIG. 2 is formed with eight scanning lines, while segmented regions obtained by dividing the second region, which is the same region as the first region, into four segments are each formed with two scanning lines.

During the scans illustrated in FIG. 3, the second ultrasound scans are performed on the first scanning line and the second scanning line in the stated order. After the second ultrasound scan is performed on the second scanning line, the first ultrasound scans are sequentially performed on the first to the eighth scanning lines in the stated order (the first ultrasound scans for the first time).

Subsequently, after the first ultrasound scans are performed for the first time, the second ultrasound scans are performed on the third scanning line and the fourth scanning line in the state order. After the second ultrasound scan is performed on the fourth scanning line, the first ultrasound scans are performed again on the first to the eighth scanning line in the stated order (the first ultrasound scans for the second time).

Subsequently, the second ultrasound scans are performed on the fifth scanning line and the sixth scanning line in the stated order, the first ultrasound scans are performed again on the first to the eighth scanning lines in the stated order (the first ultrasound scans for the third time).

Subsequently, after the second ultrasound scans are performed on the seventh scanning line and the eighth scanning line in the stated order, the first ultrasound scans are performed again on the first to the eighth scanning lines in the stated order (the first ultrasound scans for the fourth time). Also after the first ultrasound scans are performed for the fourth time, the second ultrasound scans and the first ultrasound scans are performed so as to alternate in a similar manner. In other words, in the first embodiment, the transmission and reception circuitry 110 performs the first ultrasound scans on the first region and the second ultrasound scans on parts (the segmented regions) of the second region so as to alternate.

Next, an example will be explained in which the data length of the data sequence is set to "4", while the number of overlapping data sequences (hereinafter "overlapping number") between displayed frames is set to "3". In this situation, the Doppler processing circuitry 140 generates Doppler data for the first frame, from the reflected-wave data acquired in the first ultrasound scans performed for the first time up to the fourth time. In other words, the Doppler processing circuitry 140 generates the Doppler data for the first frame from the reflected-wave data acquired in the first ultrasound scans corresponding to the four times, which correspond to the data length "4" of the data sequence. The Doppler data is data from which the blood flow image data is to be generated. Further, from the Doppler data for the first frame, the image generating circuitry 150 generates blood flow image data of the first frame. Subsequently, the controlling circuitry 180 causes the display 103 to display a blood flow image of the first frame represented by the blood flow image data of the first frame.

Subsequently, the Doppler processing circuitry 140 generates Doppler data for the second frame, from the reflected-wave data acquired in the first ultrasound scans performed for the second time up to the fifth time. In this situation, the reflected-wave data acquired in the first ultrasound scans performed for the second time up to the fifth time and the reflected-wave data acquired in the first ultrasound scans performed for the first time up to the fourth time described above overlap with each other by the reflected-wave data acquired in the first ultrasound scans performed for the second time up to the fourth time. In other words, the two pieces of reflected-wave data overlap with each other by the number corresponding to the overlapping number "3".

Subsequently, from the Doppler data for the second frame, blood flow image data of the second frame is generated. After that, the display 103 displays a blood flow image of the second frame represented by the blood flow image data of the second frame. Similarly, from the reflected-wave data acquired in the first ultrasound scans performed for the third time up to the sixth time, Doppler data for the third frame is generated. In other words, from the reflected-wave data acquired in the first ultrasound scans performed for an N-th time up to an (N+3)-th time, Doppler data for an N-th frame is generated, where N is a positive integer.

In the example illustrated in FIG. 3, the second ultrasound scans corresponding to one frame are completed when the first ultrasound scans corresponding to the four frames are completed. In the example illustrated in FIG. 3, the display mode is such that, while one frame of the blood flow image is displayed, images in the segmented regions (parts of the tissue image and parts of the contrast-enhanced image) obtained by dividing the second region into the four segments are updated.

Figure 4:
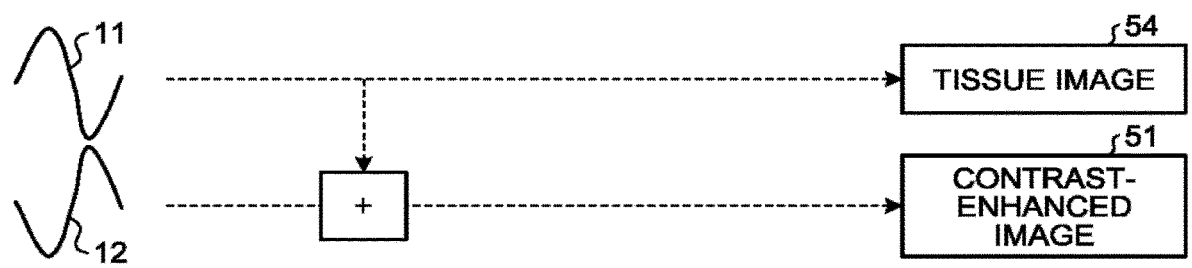
FIG. 4 is a drawing for explaining an example in which a phase modulation method is used according to the first embodiment.

Next, an example will be explained in which the phase modulation method is used in the second ultrasound scans. FIG. 4 is a drawing for explaining the example in which the phase modulation method is used according to the first embodiment. When the phase modulation method is used, with respect to the same scanning line, the transmission and reception circuitry 110 causes the ultrasound probe 101 to transmit two types of ultrasound waves, namely an ultrasound wave 11 and another ultrasound wave 12, having mutually-different polarities, as illustrated in FIG. 4.

After that, the transmission and reception circuitry 110 generates reflected-wave data based on a reflected wave of the ultrasound wave 11 and reflected-wave data based on a reflected wave of the ultrasound wave 12. Further, the B-mode processing circuitry 130 generates B-mode data (first B-mode data) from which tissue image data is to be generated, by performing an envelope detecting process or the like on the reflected-wave data based on the reflected wave of the ultrasound wave 11. Also, the B-mode processing circuitry 130 generates B-mode data (second B-mode data) from which contrast-enhanced image data is to be generated, by performing an envelope detecting process or the like on data obtained by adding the reflected-wave data based on the reflected wave of the ultrasound wave 12 to the reflected-wave data based on the reflected wave of the ultrasound wave 11. Further, the image generating circuitry 150 generates tissue image data indicating a part (a segmented region) of a tissue image 54, on the basis of the first B-mode data. Also, the image generating circuitry 150 generates contrast-enhanced image data indicating a part (a segmented region) of a contrast-enhanced image 51 rendering a non-linear signal from a contrast agent in a picture, on the basis of the second B-mode data.

Figure 5:
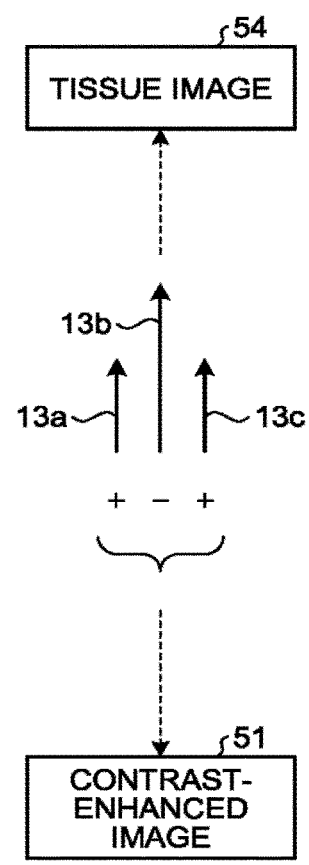
FIG. 5 is a drawing for explaining an example in which an amplitude modulation method is used according to the first embodiment.

Next, an example will be explained in which the amplitude modulation method, which is selectable, is used in the second ultrasound scans. FIG. 5 is a drawing for explaining the example in which the amplitude modulation method is used according to the first embodiment. When the amplitude modulation method is used, for example, with respect to the same scanning line, the transmission and reception circuitry 110 transmits an ultrasound wave 13a of which the amplitude is "0.5", an ultrasound wave 13b of which the amplitude is "1", and an ultrasound wave 13c of which the amplitude is "0.5" in the stated order, as illustrated in FIG. 5. In other words, the transmission and reception circuitry 110 transmits the two types of ultrasound waves, namely, the ultrasound waves 13a and 13c of which the amplitude is "0.5" and the ultrasound wave 13b of which the amplitude is "1".

Further, the B-mode processing circuitry 130 performs an addition/subtraction process on pieces of reflected-wave data each of which is based on a different one of the reflected waves of the three ultrasound waves (the two types of ultrasound waves). More specifically, the B-mode processing circuitry 130 performs the following processes where "R1" denotes the reflected-wave data based on the reflected wave of the ultrasound wave 13a; "R2" denotes the reflected-wave data based on the reflected wave of the ultrasound wave 13b; and "R3" denotes the reflected-wave data based on the reflected wave of the ultrasound wave 13c. For example, the B-mode processing circuitry 130 generates B-mode data (the second B-mode data) from which contrast-enhanced image data is to be generated, by performing an envelope detecting process or the like on data obtained by performing an addition/subtraction process expressed as "R1−R2+R3". Further, the B-mode processing circuitry 130 generates B-mode data (the first B-mode data) from which tissue image data is to be generated, by performing an envelope detecting process or the like on the reflected-wave data "R2" based on the reflected wave of the ultrasound wave 13b.

After that, the image generating circuitry 150 generates tissue image data indicating a part (a segmented region) of the tissue image 54, on the basis of the first B-mode data. Further, the image generating circuitry 150 generates contrast-enhanced image data indicating a part (a segmented region) of the contrast-enhanced image 51 rendering a non-linear signal from the contrast agent in a picture, on the basis of the second B-mode data.

In this manner, when either one of the phase modulation and the amplitude modulation methods is used, the tissue image data is generated by using the parts of the reflected-wave data acquired by the second ultrasound scans, which are the scans for acquiring the contrast-enhanced image data. In other words, the image generating circuitry 150 generates the tissue image data on the basis of the parts of the reflected-wave data acquired by the second ultrasound scans. Consequently, according to the present embodiment, it is possible to acquire the contrast-enhanced image and the tissue image, by simply performing the single type of scans called the second ultrasound scans.

Figure 6:
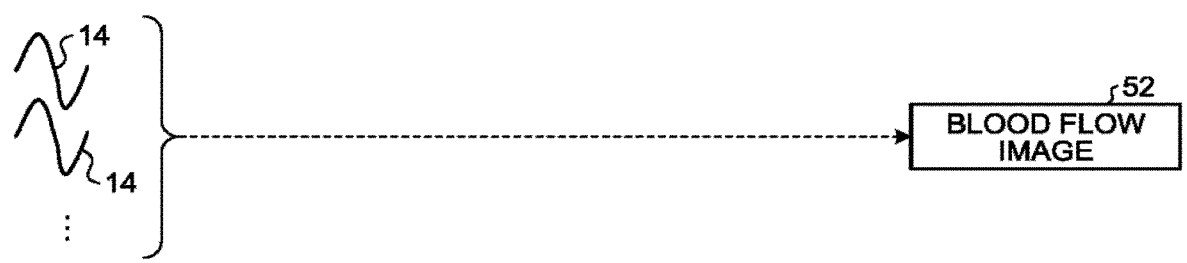
FIG. 6 is a drawing for explaining an example of the first ultrasound scans according to the first embodiment.

Next, an example of the first ultrasound scans will be explained. FIG. 6 is a drawing for explaining the example of the first ultrasound scans according to the first embodiment.

In the first ultrasound scans, the transmission and reception circuitry 110 performs, via the ultrasound probe 101, the ultrasound wave transmission and reception only once with respect to each of the scanning lines. More specifically, as the first ultrasound scans, the transmission and reception circuitry 110 transmits an ultrasound wave 14 once with respect to each of the plurality of scanning lines forming the first region and receives reflected waves of the ultrasound waves 14. Further, with respect to each of the scanning lines, the transmission and reception circuitry 110 generates reflected-wave data based on the reflected waves of the ultrasound waves 14. Further, the transmission and reception circuitry 110 repeatedly performs the process of generating reflected-wave data in this manner as many times as a plurality of frames. After that, the Doppler processing circuitry 140 estimates blood flow information on the basis of the reflected-wave data based on the reflected waves of the ultrasound waves 14 corresponding to the plurality of frames. Further, the Doppler processing circuitry 140 generates Doppler data indicating the estimated blood flow information. After that, on the basis of the Doppler data, the image generating circuitry 150 generates blood flow image data representing a blood flow image 52.

Next, an example of a method for generating an MTI filter matrix according to the first embodiment will be explained. The Doppler processing circuitry 140 at first calculates a correlation matrix of a scanned range, from a data sequence including consecutive pieces of reflected-wave data in mutually the same position acquired by repeating the scanning mode in which the ultrasound wave is transmitted and received once with respect to each of the scanning lines in the first region formed by the plurality of scanning lines.

More specifically, the Doppler processing circuitry 140 calculates a correlation matrix "$R_{xx}$" by using Expression (1) presented below.

$$R_{xx} = \frac{1}{M} \sum_{m=1}^{M} x_m x_m^H \quad (1)$$

In this situation, "$x_m$" in Expression (1) is a column vector expressing the data sequence in a position "m". The length "L" of the column vector "$x_m$" is a data length used for the calculation to estimate the Doppler data (the blood flow information) in one frame. For example, in the example in FIG. 3, "L" is equal to "4". Further, in Expression (1), "$x_m^H$" denotes a transposed matrix of a matrix taking complex conjugates of the elements of "$x_m$".

In this situation, the position "m" denotes the position of a sampling point set in the entire space in which the high framerate ultrasound scan is performed. The position "m" is expressed in a two-dimensional coordinate system when a two-dimensional scan is performed and is expressed in a three-dimensional coordinate system when a three-dimensional scan is performed. Further, "M" in Expression (1) denotes the total quantity of "m".

In other words, by using Expression (1), the Doppler processing circuitry 140 is configured to calculate an autocorrelation matrix of the data sequence at each of a plurality of sampling points and to calculate an average of autocorrelation matrices of the plurality of sampling points. As a result, the Doppler processing circuitry 140 calculates a correlation matrix of the first region. From Expression (1), the correlation matrix "$R_{xx}$" is a matrix having L lines and L columns. In this situation, as explained above, it is possible to arbitrarily change the data length "L" of the data sequence of which the correlation matrix is calculated. Further, the data sequence of which the correlation matrix is calculated may be set so as to overlap between displayed frames.

Further, the Doppler processing circuitry 140 calculates eigenvalues of the correlation matrix and eigenvectors corresponding to the eigenvalues. In other words, the Doppler processing circuitry 140 calculates L sets of eigenvalues and eigenvectors from the correlation matrix "$R_{xx}$". Further, the Doppler processing circuitry 140 sets a matrix "V" by arranging the "L" eigenvectors on the basis of the magnitudes of the eigenvalues. After that, the Doppler processing circuitry 140 calculates a matrix obtained by reducing the rank of the matrix "V", as an MTI filter matrix used for suppressing the clutter component. The Doppler processing circuitry 140 obtains the matrix "V" by using the "L" eigenvectors as "L" column vectors and arranging the "L" column vectors in descending order of the eigenvalues thereof and further calculates an MTI filter matrix "W" by using Expression (2) presented below.

$$W = V \begin{pmatrix} 0 & & & \\ & 0 & & \\ & & \ddots & \\ & & & 1 \\ & & & & 1 \end{pmatrix} V^H \quad (2)$$

In Expression (2), "$V^H$" denotes a complex conjugate transpose matrix of "V". Further, on the right-hand side of Expression (2), the matrix between "V" and "$V^H$" is a diagonal matrix having L lines and L columns. From Expression (2), the MTI filter matrix "W" is a matrix having L lines and L columns. In this situation, the value by which the rank is to be reduced is determined by how many diagonal elements in the diagonal matrix having the L lines and the L columns are to be changed to "0". In the following sections, the value by which the rank is to be reduced will be referred to as a "Rank Cut Value".

A column vector (an eigenvector) having a large eigenvalue corresponds to a clutter component that has a small frequency shift caused by the Doppler effect, i.e., that has low moving velocity, in a Doppler scanned range. According to Expression (2), a matrix is calculated by reducing the rank of the matrix "V" by eliminating as many components as the Rank Cut Value starting with components having larger eigenvalues and further inversely transforming the matrix by using "$V^H$". By using Expression (2), it is possible to obtain the MTI filter matrix "W" that functions as a high-pass filter to eliminate moving components (the clutter component) of the tissue.

In this situation, for example, the Doppler processing circuitry 140 determines the Rank Cut Value on the basis of a value set in advance or a value designated by the operator. In the manner described above, the adaptive MTI filter is generated. In other words, with respect to each of the positions in the first region, the Doppler processing circuitry 140 is configured to obtain a data sequence acquired from the first ultrasound scans performed multiple times and is configured to generate the adaptive MTI filter on the basis of the data sequences. Further, the Doppler processing circuitry 140 is configured to obtain the blood flow information by inputting the data sequences to the generated adaptive MTI filter. Further, the image generating circuitry 150 is configured to generate the blood flow image data on the basis of the blood flow information obtained by the Doppler processing circuitry 140.

Figure 7:
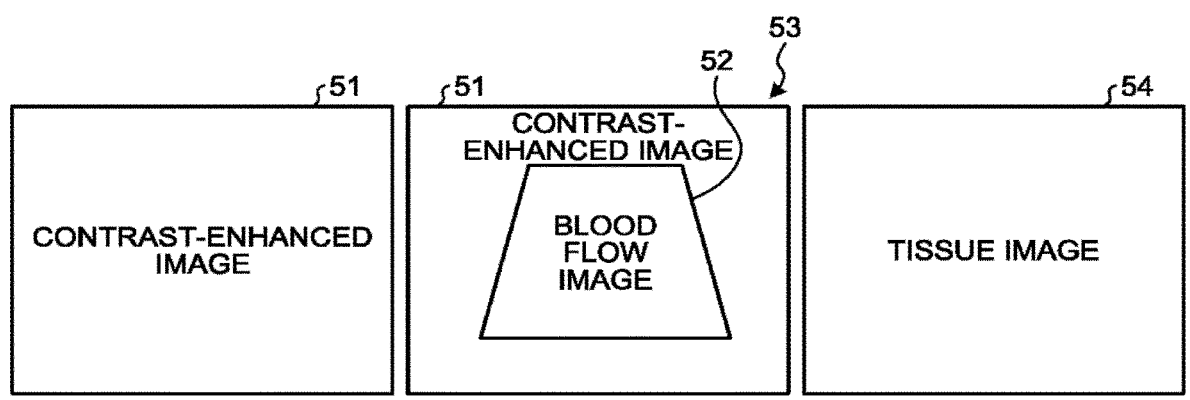
FIG. 7 is a drawing for explaining an example of an image display mode according to the first embodiment.

Next, an example of an image display mode according to the first embodiment will be explained. FIG. 7 is a drawing for explaining the example of the image display mode according to the first embodiment. As illustrated in FIG. 7, in the first embodiment, the controlling circuitry 180 causes the display 103 to display the contrast-enhanced image 51, a superimposed image 53 in which the blood flow image 52 is superimposed on the contrast-enhanced image 51, and the tissue image 54 that are arranged along the left-and-right direction. Further, the controlling circuitry 180 causes the display 103 to display the contrast-enhanced image 51, the superimposed image 53, and the tissue image 54 simultaneously. FIG. 7 illustrates the example in which the area of the second region is larger than the area of the first region.

In this situation, the controlling circuitry 180 may cause the display 103 to display, in a real-time manner, the contrast-enhanced image 51, the superimposed image 53, and a tissue image simultaneously. Alternatively, as a post-processing process, the controlling circuitry 180 may cause the display 103 to display the contrast-enhanced image 51, the superimposed image 53, and a tissue image simultaneously.

When various types of images are displayed in a real-time manner, the following processes are performed as processes performed by the entire ultrasound diagnosis apparatus 1: For example, every time a reflected-wave signal is received from the ultrasound probe 101, the transmission and reception circuitry 110 generates reflected-wave data on the basis of the received reflected-wave signal. Further, every time reflected-wave data is generated by the transmission and reception circuitry 110, the B-mode processing circuitry 130 generates B-mode data on the basis of the reflected-wave data. Further, every time reflected-wave data is generated by the transmission and reception circuitry 110, the Doppler processing circuitry 140 generates Doppler data on the basis of the reflected-wave data.

Further, every time B-mode data is generated by the B-mode processing circuitry 130, the image generating circuitry 150 generates B-mode image data (contrast-enhanced image data and tissue image data) on the basis of the B-mode data.

Further, every time Doppler data is generated by the Doppler processing circuitry 140, the image generating circuitry 150 generates Doppler image data (blood flow image data) on the basis of the Doppler data. In this situation, on the basis of one piece of B-mode data based on the second ultrasound scan from one time, the image generating circuitry 150 only generates either contrast-enhanced image data being a part of the contrast-enhanced image 51 or tissue image data being a part of the tissue image 54. Further, on the basis of a plurality of pieces of B-mode data based on a plurality of second ultrasound scans (equal to the number of segmented regions obtained by dividing the second region), the image generating circuitry 150 generates either the contrast-enhanced image data of the entire contrast-enhanced image 51 or the tissue image data of the entire tissue image 54. In other words, the image generating circuitry 150 is configured to generate the contrast-enhanced image 51 and the tissue image 54 based on the results of the plurality of second ultrasound scans.

Further, every time contrast-enhanced image data and tissue image data are generated by the image generating circuitry 150, the controlling circuitry 180 causes the display 103 to display a part of the contrast-enhanced image 51 represented by the contrast-enhanced image data and a part of the tissue image 54 represented by the tissue image data and updates the part of the contrast-enhanced image 51 and the part of the tissue image 54.

Further, every time contrast-enhanced image data and blood flow image data are generated, the image generating circuitry 150 generates superimposed image data by superimposing the contrast-enhanced image data on the blood flow image data. Further, every time superimposed image data is generated by the image generating circuitry 150, the controlling circuitry 180 causes the display 103 to display the superimposed image 53 represented by the superimposed image data.

Further, when various types of images are displayed as a post-processing process, the following processes are performed as processes performed by the entire ultrasound diagnosis apparatus 1: For example, the controlling circuitry 180 reads the blood flow image data, the contrast-enhanced image data, and the tissue image data from the image memory 160. Further, the controlling circuitry 180 outputs the contrast-enhanced image data and the blood flow image data to the image generating circuitry 150. When having received the contrast-enhanced image data and the blood flow image data, the image generating circuitry 150 generates superimposed image data by superimposing the contrast-enhanced image data on the blood flow image data.

Subsequently, the controlling circuitry 180 causes the display 103 to display the contrast-enhanced image 51 represented by the contrast-enhanced image data, the superimposed image 53 represented by the superimposed image data, and the tissue image 54 represented by the tissue image data.

Figure 8:
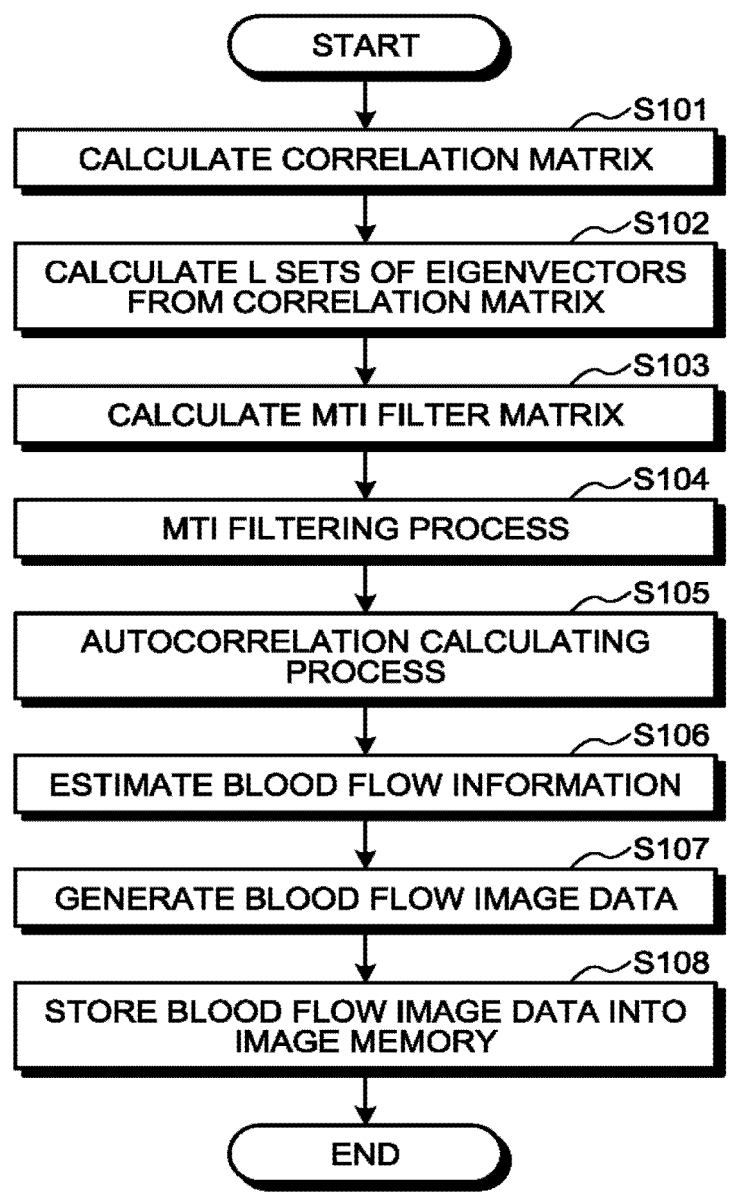
FIG. 8 is a flowchart for explaining an example of a flow in a first generating process performed by Doppler processing circuitry and image generating circuitry according to the first embodiment.

Next, an example of a flow in a first generating process to generate blood flow image data will be explained, with reference to FIG. 8. FIG. 8 is a flowchart for explaining the example of the flow in the first generating process performed by the Doppler processing circuitry 140 and the image generating circuitry 150 according to the first embodiment. The first generating process is performed when reflected-wave data corresponding to a number of scan frames (corresponding to the data length) subject to processing has been stored in the buffer memory 120. Further, the first generating process is also performed every time a new piece of reflected-wave data is stored into the buffer memory 120 by the transmission and reception circuitry 110, while the buffer memory 120 has stored therein reflected-wave data corresponding to the data length.

As illustrated in FIG. 8, the Doppler processing circuitry 140 calculates a correlation matrix of the first region (step S101). After that, the Doppler processing circuitry 140 calculates L sets of eigenvalues and eigenvectors from the correlation matrix (step S102).

Subsequently, on the basis of the L sets of eigenvalues and eigenvectors, the Doppler processing circuitry 140 calculates an MTI filter matrix (step S103). After that, the Doppler processing circuitry 140 performs an MTI filtering process on pieces of reflected-wave data corresponding to the data length that are in mutually the same position (step S104). Further, by using the output data output from the MTI filtering process, the Doppler processing circuitry 140 performs an autocorrelation calculating process (step S105). After that, the Doppler processing circuitry 140 estimates blood flow information from a result of the autocorrelation calculating process and further generates Doppler data indicating the blood flow information (step S106).

Subsequently, the image generating circuitry 150 generates blood flow image data from the Doppler data indicating the blood flow information (step S107). In other words, the image generating circuitry 150 generates the blood flow image based on results of the first ultrasound scans performed multiple times in mutually the same position within the first region, so as to have the second ultrasound scan performed in-between. In this manner, at step S107, the image generating circuitry 150 generates the blood flow image corresponding to one image frame by implementing the Doppler method, on the basis of the data sequence including the pieces of reception data obtained from the first ultrasound scans performed multiple times. In this situation, the blood flow image corresponding to the one image frame is not an image generated from reflected-wave data of an acquired frame in a single temporal phase, but is an image generated from the plurality of pieces of reflected-wave data of a plurality of acquired frames in a plurality of temporal phases. Subsequently, the image generating circuitry 150 stores the blood flow image data into the image memory 160 (step S108) and ends the first generating process. The blood flow image data generated in this manner is read by the controlling circuitry 180 and is displayed as a blood flow image on the display 103.

Figure 9:
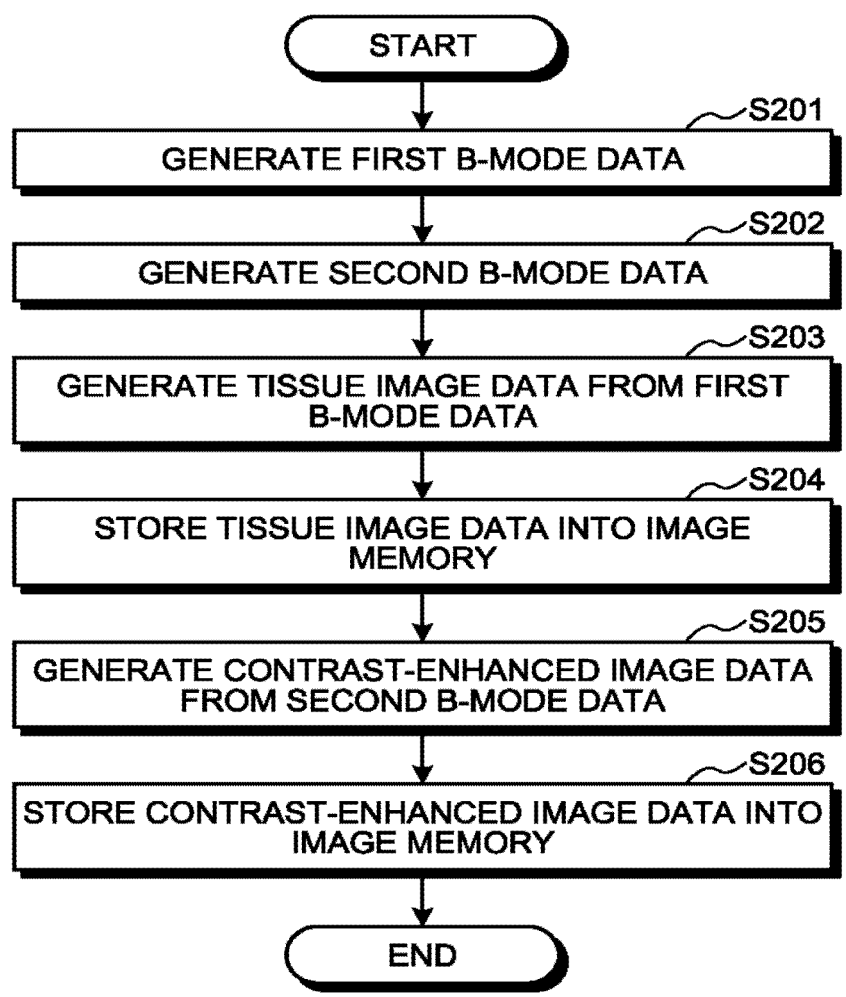
FIG. 9 is a flowchart for explaining an example of a flow in a second generating process performed by B-mode processing circuitry and the image generating circuitry according to the first embodiment.

Next, an example of a flow in a second generating process to generate the tissue image data and the contrast-enhanced image data will be explained, with reference to FIG. 9. FIG. 9 is a flowchart for explaining the example of the flow in the second generating process performed by the B-mode processing circuitry 130 and the image generating circuitry 150 according to first embodiment. The second generating process is performed with the same timing as that of the first generating process.

As illustrated in FIG. 9, the B-mode processing circuitry 130 generates first B-mode data from which the tissue image data is to be generated (step S201). After that, the B-mode processing circuitry 130 generates second B-mode data from which the contrast-enhanced image data is to be generated (step S202).

Subsequently, the image generating circuitry 150 generates tissue image data from the first B-mode data (step S203). After that, the image generating circuitry 150 stores the tissue image data into the image memory 160 (step S204).

Further, the image generating circuitry 150 generates contrast-enhanced image data from the second B-mode data (step S205). After that, the image generating circuitry 150 stores the contrast-enhanced image data into the image memory 160 (step S206) and ends the second generating process.

The ultrasound diagnosis apparatus 1 according to the first embodiment has thus been explained. In the first embodiment, it is possible, as explained above, to improve the framerate of the blood flow image. Further, according to the first embodiment, in the second ultrasound scans to acquire the contrast-enhanced image, the tissue image is also acquired in addition to the contrast-enhanced image. For this reason, according to the first embodiment, because there is no need to perform an ultrasound scan to acquire the tissue image alone, it is also possible to improve the framerates of the contrast-enhanced image and the tissue image. Consequently, by using the ultrasound diagnosis apparatus 1 according to the first embodiment, it is possible to acquire, in an excellent manner, at least two selected from among the blood flow image, the contrast-enhanced image, and the tissue image.

Further, as illustrated at steps S108, S204, and S206, the image generating circuitry 150 is configured to store, into the image memory 160, the blood flow image data, the tissue image data, and the contrast-enhanced image data independently of each other. For example, even when the display 103 is displaying two types of images selected from among the blood flow image, the tissue image, and the contrast-enhanced image, the three types of image data are saved in the image memory 160 as browsing-purpose image data, as explained above. According to the first embodiment, because the various types of browsing-purpose image data are saved in the image memory 160, when the operator wishes to browse any of the various types of images, the operator is able to cause the display 103 to display the desired image anytime.

Patent Literature 2 (Japanese Laid-open Patent Publication No. 2009-119134) indicates that contrast-enhanced mode image information, B-mode image information, and CFM image information are formed by using a reception echo sequence obtained from ultrasound wave transmissions and receptions performed multiple times. However, because a generally-used CFM method is used in Patent Literature 2 (International Publication No. 2014/115782), it would be difficult to detect blood flow information related to a blood flow having a low flowrate, unlike the ultrasound diagnosis apparatus 1 according to the first embodiment. Further, when the amplitude modulation method is applied to the technique described in Patent Literature 1 in the same manner as in the ultrasound diagnosis apparatus 1 according to the first embodiment, there is a possibility that CFM image information may be affected.

First Modification Example of First Embodiment

In the first embodiment, the example is explained in which the transmission and reception circuitry 110 performs the scan on a part (a segmented region) of the second region, in the second ultrasound scan at one time. However, the transmission and reception circuitry 110 may perform a scan on the entire second region in the second ultrasound scan at one time. Thus, this modification example will be explained as a first modification example of the first embodiment.

For example, when the size of the second region is relatively small, and the number of scanning lines forming the second region is relatively small, the transmission and reception circuitry 110 may perform a scan on the entire second region in the second ultrasound scan at one time. Further, when it is possible to scan the entire second region by transmitting a plane wave or a converged wave having a large width as the ultrasound wave, the transmission and reception circuitry 110 may perform a scan on the entire second region by transmitting a plane wave or a converged wave in the second ultrasound scan at one time. In other words, it is sufficient when the transmission and reception circuitry 110 performs the first ultrasound scans on the first region and the second ultrasound scans on at least a part of the second region, so as to alternate. In that situation, it is sufficient when the image generating circuitry 150 generates the contrast-enhanced image 51 and the tissue image 54 based on a result of the second ultrasound scan performed at least one time.

Second Modification Example of First Embodiment

Further, in the first embodiment, the example is explained in which the scan on the segmented region is performed in the second ultrasound scan at one time. However, the region scanned in the second ultrasound scan at one time is not limited to a segmented region. Thus, another example will be explained as a second modification example of the first embodiment.

For example, in the second modification example, in the second ultrasound scan at one time, a scan may be performed on each of a plurality of regions entirely covering the second region. In this situation, in the second modification example, two regions positioned adjacent to each other partially overlaps with each other.

Third Modification Example of First Embodiment

Further, in the first embodiment, the example is explained in which, for the second ultrasound scans, the operator selects one from between the phase modulation method and the amplitude modulation method. However, another arrangement is acceptable in which the controlling circuitry 180 selects one from between the phase modulation method and the amplitude modulation method. Thus, this modification example will be explained as a third modification example of the first embodiment.

In the third modification example, for instance, the controlling circuitry 180 selects one from between the phase modulation method and the amplitude modulation method, in accordance with a flowrate range. In this situation, the flowrate range is a range of flowrate values of a blood flow that can be expressed in a blood flow image being a color Doppler image. In other words, the flowrate range is a range of flowrate values of a blood flow which the ultrasound diagnosis apparatus 1 is able to detect. The operator is able to set the flowrate range by, for example, operating the input device 102. For example, when the upper limit value of the flowrate range is equal to or larger than a predetermined threshold value, the controlling circuitry 180 selects the amplitude modulation method. On the contrary, when the upper limit value of the flowrate range is smaller than the predetermined threshold value, the controlling circuitry 180 selects the phase modulation method. Further, in the second ultrasound scans, the transmission and reception circuitry 110 transmits ultrasound waves on the basis of the selected method. In this situation, the controlling circuitry 180 may vary the number of segmented regions into which the second region is to be divided, depending on whether the phase modulation method is selected or the amplitude modulation method is selected.

Further, the controlling circuitry 180 may vary the intervals "T" at which the first ultrasound scans are performed illustrated in FIG. 2 explained earlier, in accordance with the flowrate range. For example, when the operator wishes to observe a blood flow having a lower flowrate (e.g., a flowrate equal to or lower than a specific flowrate such as 0.5 cm/s), the operator may change the flowrate range so as to decrease the lower limit value of the flowrate range. In that situation, to detect the blood flow having the lower flowrate, the intervals "T" need to be longer. Accordingly, the controlling circuitry 180 changes the intervals "T" in such a manner that the smaller the lower limit value of the flowrate range is, the longer are the intervals "T". Further, the controlling circuitry 180 controls the transmission circuitry 110a so that the ultrasound probe 101 performs the first ultrasound scans at the post-change intervals "T". With this arrangement, it is possible to properly change the intervals "T" at which the first ultrasound scans are performed in accordance with the lower limit value of the flowrate range, so as to enable the operator to view a blood flow image indicating blood flow information about the blood flow having the lower blood flowrate.

Fourth Modification Example of First Embodiment

Next, a fourth modification example of the first embodiment will be explained. In the fourth modification example, examples of other image display modes will be explained, which are different from the image display mode explained in the first embodiment with reference to FIG. 7. It is possible to display the various types of images explained in the fourth modification example, in a real-time manner or as a post-processing process, in the same manner as explained in the first embodiment.

Figure 10:
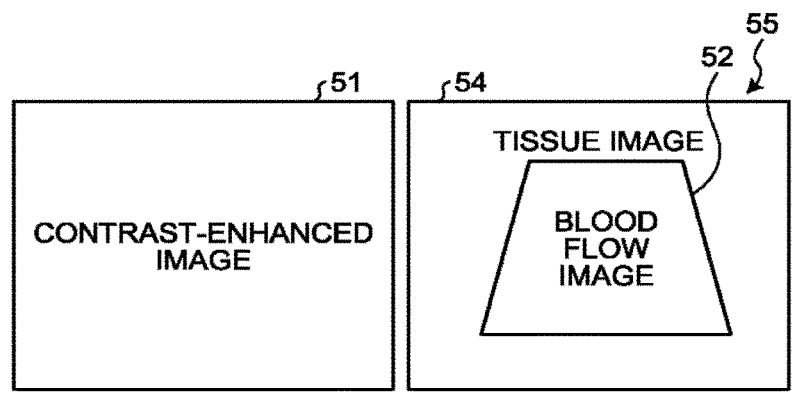
FIG. 10 is a drawing for explaining an example of another image display mode according to a fourth modification example of the first embodiment.
Figure 11:
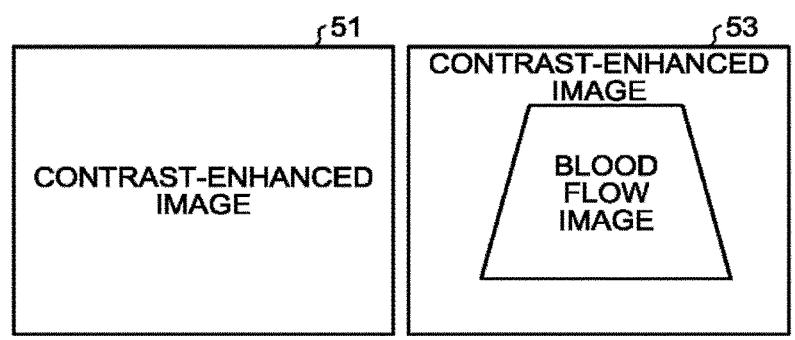
FIG. 11 is a drawing for explaining an example of yet another image display mode according to the fourth modification example of the first embodiment.

FIGS. 10 to 29 are drawings for explaining the examples of the other image display modes according to the fourth modification example of the first embodiment. As illustrated in FIG. 10, the controlling circuitry 180 may cause the display 103 to display the contrast-enhanced image 51 and a superimposed image 55 in which the blood flow image 52 is superimposed on the tissue image 54 that are arranged along the left-and-right direction. Further, as illustrated in FIG. 11, the controlling circuitry 180 may cause the display 103 to display the contrast-enhanced image 51 and the superimposed image 53 that are arranged along the left-and-right direction.

Figure 12:
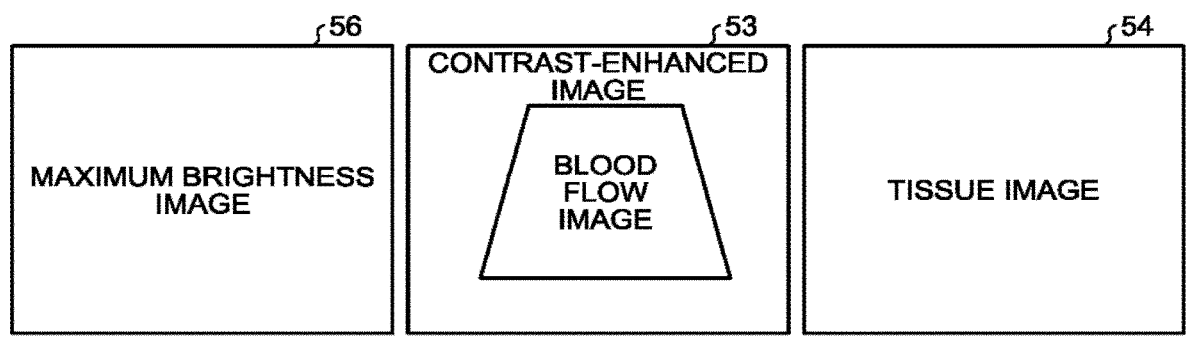
FIG. 12 is a drawing for explaining an example of yet another image display mode according to the fourth modification example of the first embodiment.

In another example, as illustrated in FIG. 12, the controlling circuitry 180 may cause the display 103 to display a maximum brightness image 56, the superimposed image 53, and the tissue image 54 that are arranged along the left-and-right direction. In this situation, the maximum brightness image 56 is generated by the image generating circuitry 150. For example, by using a Micro Flow Imaging (MFI) method by which structures of small blood flows can clearly be rendered in a picture, the image generating circuitry 150 generates the maximum brightness image 56. More specifically, the image generating circuitry 150 performs a maximum brightness retaining calculation (a maximum value retaining calculation) on a plurality of contrast-enhanced images 51, further selects a maximum brightness level for each of the pixels from among the plurality of contrast-enhanced images 51, and generates the maximum brightness image 56 in which each of the pixels is displayed with the selected maximum brightness level. In this situation, according to the MFI method, the transmission and reception circuitry 110 sweeps away air bubbles (bubbles) by transmitting an ultrasound wave having high sound pressure (which may be called a flash), so that the image generating circuitry 150 renders a reperfusion in a picture. In this situation, the operator selects whether or not the ultrasound wave having the high sound pressure is to be transmitted.

Figure 13:
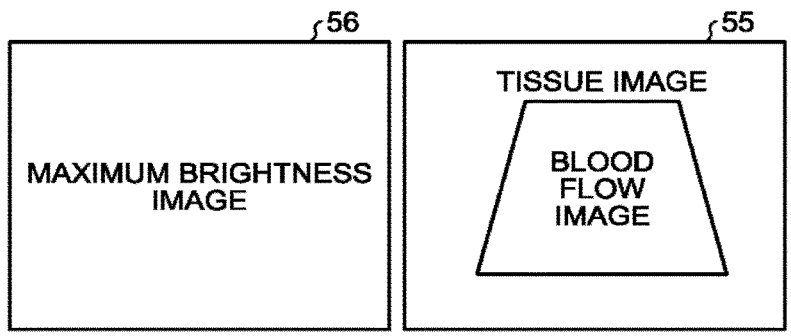
FIG. 13 is a drawing for explaining an example of yet another image display mode according to the fourth modification example of the first embodiment.
Figure 14:
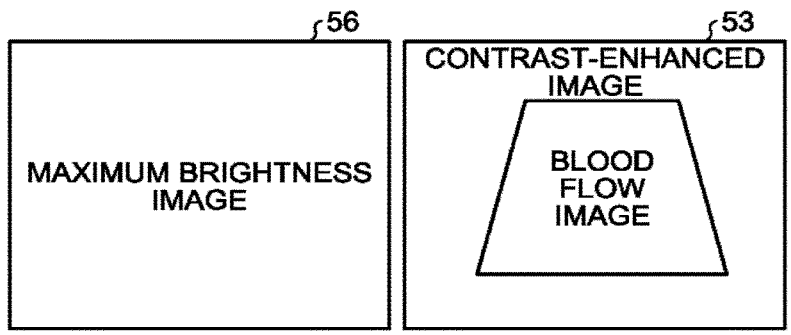
FIG. 14 is a drawing for explaining an example of yet another image display mode according to the fourth modification example of the first embodiment.

In yet another example, as illustrated in FIG. 13, the controlling circuitry 180 may cause the display 103 to display the maximum brightness image 56 and the superimposed image 55 that are arranged along the left-and-right direction. In yet another example, as illustrated in FIG. 14, the controlling circuitry 180 may cause the display 103 to display the maximum brightness image 56 and the superimposed image 53 that are arranged along the left-and-right direction.

Figure 15:
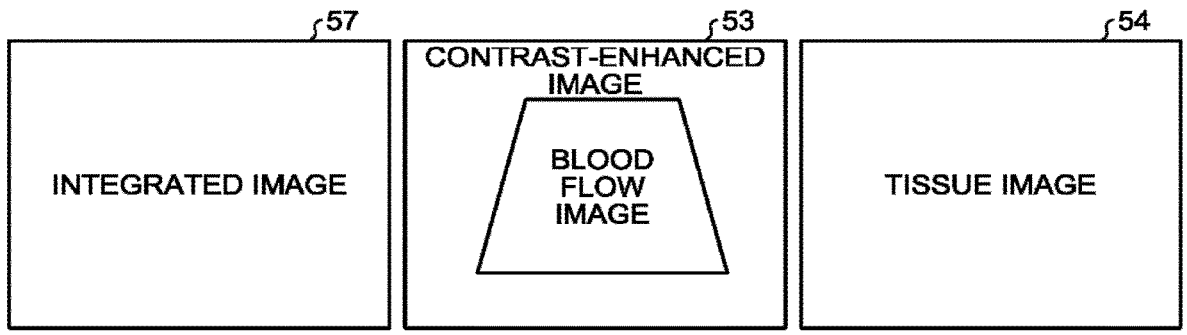
FIG. 15 is a drawing for explaining an example of yet another image display mode according to the fourth modification example of the first embodiment.

In yet another example, as illustrated in FIG. 15, the controlling circuitry 180 may cause the display 103 to display an integrated image 57, the superimposed image 53, and the tissue image 54 that are arranged along the left-and-right direction. In this situation, the integrated image 57 is generated by the image generating circuitry 150. For example, the image generating circuitry 150 generates the integrated image 57 by integrating a plurality of contrast-enhanced images 51 in a time direction.

Figure 16:
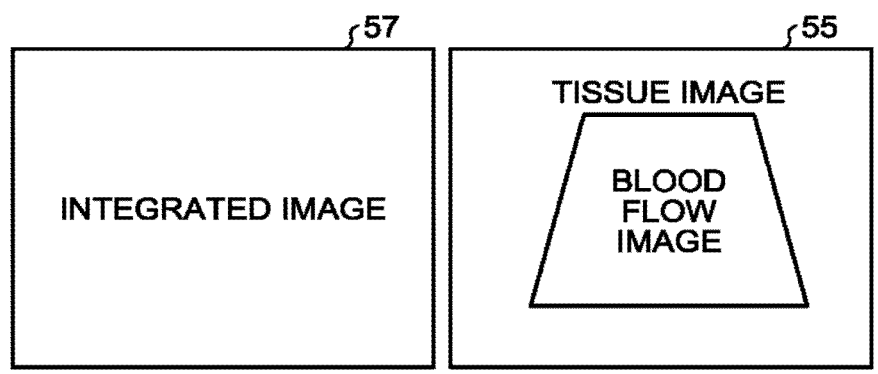
FIG. 16 is a drawing for explaining an example of yet another image display mode according to the fourth modification example of the first embodiment.
Figure 17:
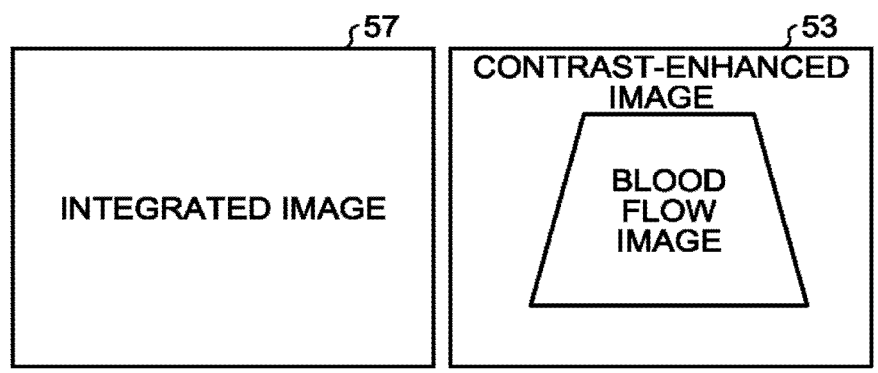
FIG. 17 is a drawing for explaining an example of yet another image display mode according to the fourth modification example of the first embodiment.

In yet another example, as illustrated in FIG. 16, the controlling circuitry 180 may cause the display 103 to display the integrated image 57 and the superimposed image 55 that are arranged along the left-and-right direction. In yet another example, as illustrated in FIG. 17, the controlling circuitry 180 may cause the display 103 to display the integrated image 57 and the superimposed image 53 that are arranged along the left-and-right direction.

Figure 18:
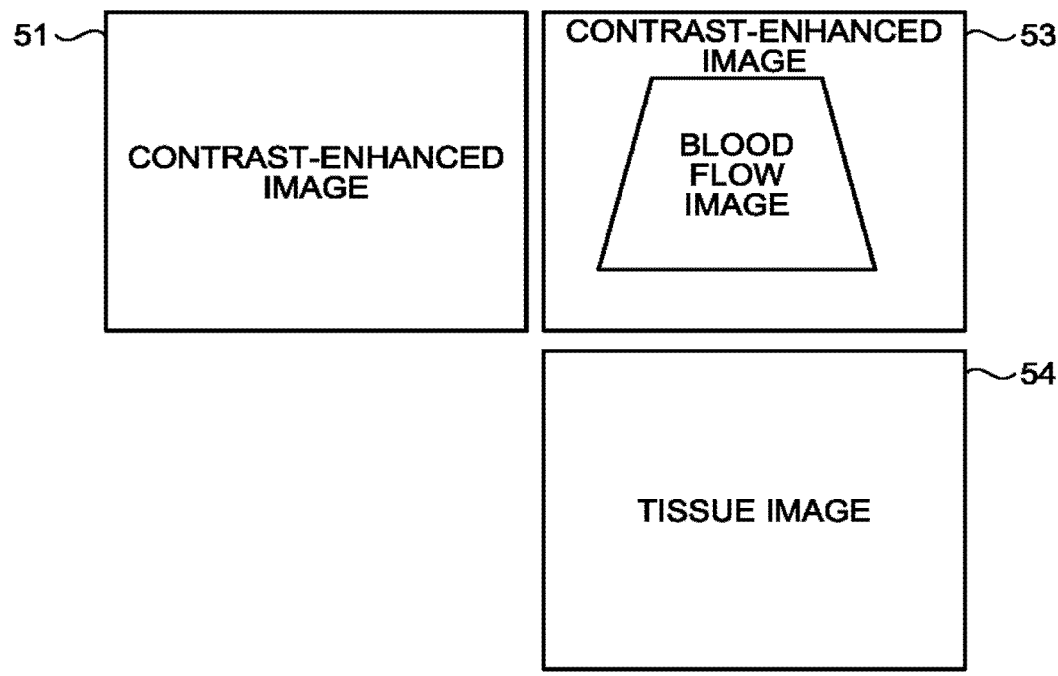
FIG. 18 is a drawing for explaining an example of yet another image display mode according to the fourth modification example of the first embodiment.

In yet another example, as illustrated in FIGS. 18 to 29, the controlling circuitry 180 may cause the display 103 to display any of the various types of images that are arranged in a matrix formation. For example, as illustrated in FIG. 18, the controlling circuitry 180 sets, in a display region of the display 103, four regions so that two images can be arranged in the left-and-right direction, while two images can be arranged in the up-and-down direction. In the following explanations, on the drawing page, the region in the upper left position will be referred to as an upper left region; the region in the upper right position will be referred to as an upper right region; the region in the lower left position will be referred to as a lower left region; and the region in the lower right position will be referred to as a lower right region.

Further, as illustrated in FIG. 18, the controlling circuitry 180 may exercise control so that the display 103 displays the contrast-enhanced image 51 in the upper left region, the superimposed image 53 in the upper right region, and the tissue image 54 in the lower right region.

Figure 19:
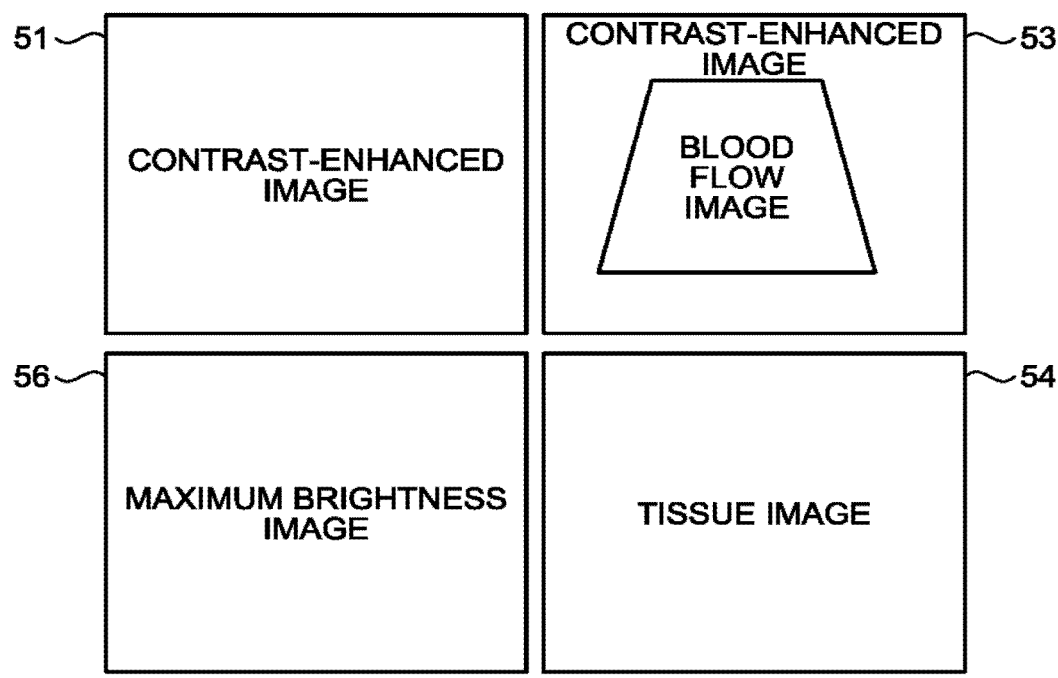
FIG. 19 is a drawing for explaining an example of yet another image display mode according to the fourth modification example of the first embodiment.

In another example, as illustrated in FIG. 19, the controlling circuitry 180 may exercise control so that the display 103 further displays the maximum brightness image 56 in the lower left region, in addition to the display state illustrated in FIG. 18.

Figure 20:
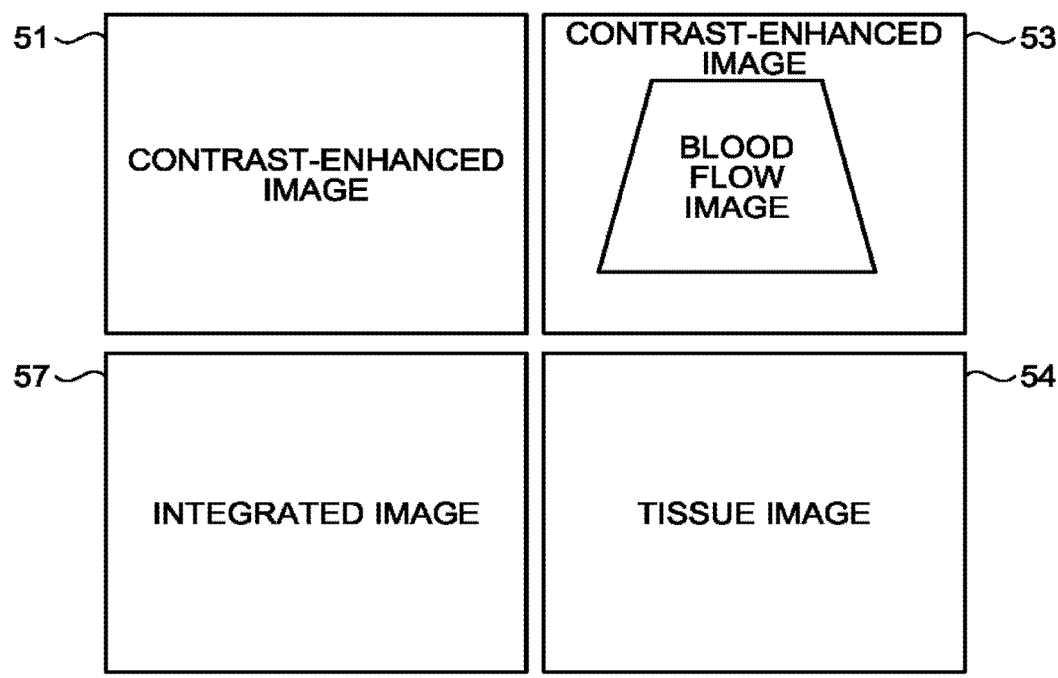
FIG. 20 is a drawing for explaining an example of yet another image display mode according to the fourth modification example of the first embodiment.

In yet another example, as illustrated in FIG. 20, the controlling circuitry 180 may exercise control so that the display 103 displays the integrated image 57 in place of the maximum brightness image 56 displayed in the lower left region in FIG. 19.

Figure 21:
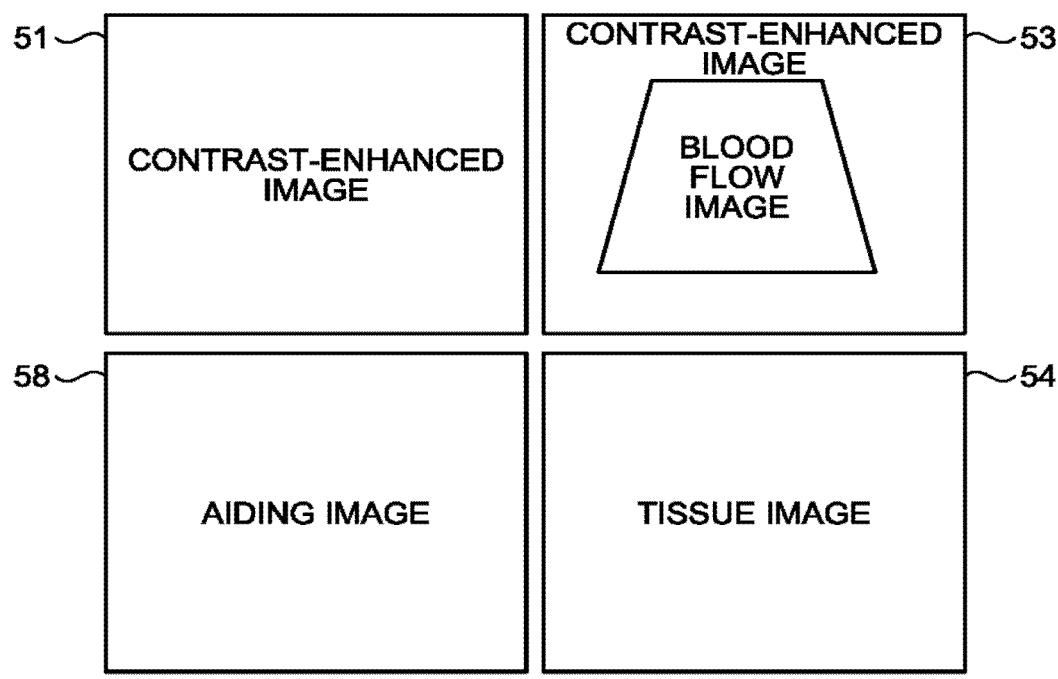
FIG. 21 is a drawing for explaining an example of yet another image display mode according to the fourth modification example of the first embodiment.

In yet another example, as illustrated in FIG. 21, the controlling circuitry 180 may exercise control so that the display 103 displays an aiding image 58 in place of the maximum brightness image 56 displayed in the lower left region in FIG. 19. In this situation, the aiding image 58 is an image used for aiding the operator such as a medical doctor or a clinical technologist in operating the ultrasound diagnosis apparatus 1 and in performing a medical examination while using the ultrasound diagnosis apparatus 1. The aiding image 58 is generated by the image generating circuitry 150.

For example, the image generating circuitry 150 performs a predetermined measuring process on a site of the subject P rendered in at least one of the contrast-enhanced image 51, the tissue image 54, and the blood flow image 52 and further generates the aiding image 58 indicating a result of the measuring process. When the measuring process is performed, in the present modification example, it is possible to use, as measuring cursors, three cursors (triple cursors) that move at the same time in the contrast-enhanced image 51, the tissue image 54, and the blood flow image 52 in synchronization with one another. Further, when there are four images in which the measuring process is to be performed, it is similarly possible to use four cursors (quad cursors) that move in the four images at the same time in synchronization with one another.

As the aiding image 58, the image generating circuitry 150 may generate an image indicating a procedure of a medical examination. Further, as the aiding image 58, the image generating circuitry 150 may generate an image indicating an image quality condition of at least one of the first and the second ultrasound scans.

Figure 22:
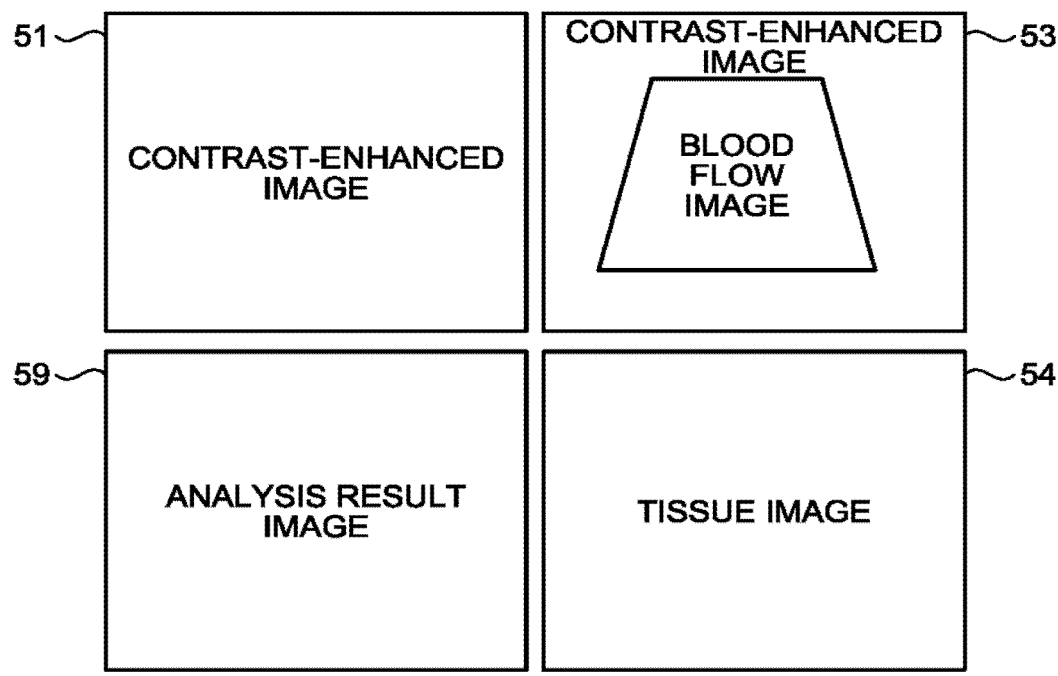
FIG. 22 is a drawing for explaining an example of yet another image display mode according to the fourth modification example of the first embodiment.

In yet another example, as illustrated in FIG. 22, the controlling circuitry 180 may exercise control so that the display 103 displays an analysis result image 59 in place of the maximum brightness image 56 displayed in the lower left region in FIG. 19. In this situation, the analysis result image 59 is an image indicating a result of an analysis (an analysis result) performed on at least one of the contrast-enhanced image 51, the tissue image 54, and the blood flow image 52. The analysis result image 59 is generated by the image generating circuitry 150.

For example, as an analysis performed on a plurality of contrast-enhanced images 51 or a plurality of blood flow images 52 in a time direction, the image generating circuitry 150 may perform a Time Curve Analysis (TCA). In the TCA, for example, temporal changes are observed in the density of a contrast agent in an analyzed region such as a region of interest, so as to generate a graph indicating the temporal changes in the density of the contrast agent or to recognize a tumor on the basis of the temporal changes in the density of the contrast agent. By performing the TCA, the image generating circuitry 150 generates, as the analysis result image 59, an image exhibiting the graph indicating the temporal changes in the density of the contrast agent or generates an image indicating a result of the recognition of the tumor.

Further, for example, the image generating circuitry 150 may generate the analysis result image 59 by implementing a parametric imaging method. The parametric imaging method is an image expressing method by which blood flow information acquired with an injection of a contrast agent is expressed by using one or more predetermined parameter values. For example, by implementing the parametric imaging method, the image generating circuitry 150 calculates a Time Density Curve (TDC) of the contrast agent for each of the pixels in the contrast-enhanced image 51 and further calculates various types of parameter values by using the calculated TDC. In this situation, as the parameter values for the parametric imaging method, for example, a Time To Peak (TTP) value indicating the time period until a peak in the TDC, a Peak Height (PH), an Area Under Curve (AUC) indicating an area of the TDC, Arrival Time (AT) of the contrast agent, a Wash Out time period from the peak to the time when the contrast agent is completely washed out, and Mean Transit Time (MTT), or the like may be calculated. Further, by implementing the parametric imaging method, the image generating circuitry 150 calculates, for each of the pixels, at least one parameter value corresponding to the blood flow information desired by the viewer and further generates, as the analysis result image 59, an image in which the pixels in the image are expressed in color by using colors corresponding to the calculated parameter values.

Further, for example, by using the technique described in Japanese Laid-open Patent Publication No. 2018-15155, the image generating circuitry 150 may generate, as the analysis result image 59, an image that quantitatively indicates a flowing direction and moving velocity of the contrast agent, by tracking (following) each of microbubbles used as the contrast agent.

For example, the image generating circuitry 150 specifies the position of the contrast agent in one contrast-enhanced image 51 (a first contrast-enhanced image) corresponding to one temporal phase and another contrast-enhanced image 51 (a second contrast-enhanced image) corresponding to another temporal phase. Further, on the basis of the position of the contrast agent in each of the first and the second contrast-enhanced images, the image generating circuitry 150 calculates a vector expressing the moving of the contrast agent. After that, the image generating circuitry 150 generates, as the analysis result image 59, a superimposed image in which an indicator having a shape of the vector is superimposed on the tissue image 54.

Figure 23:
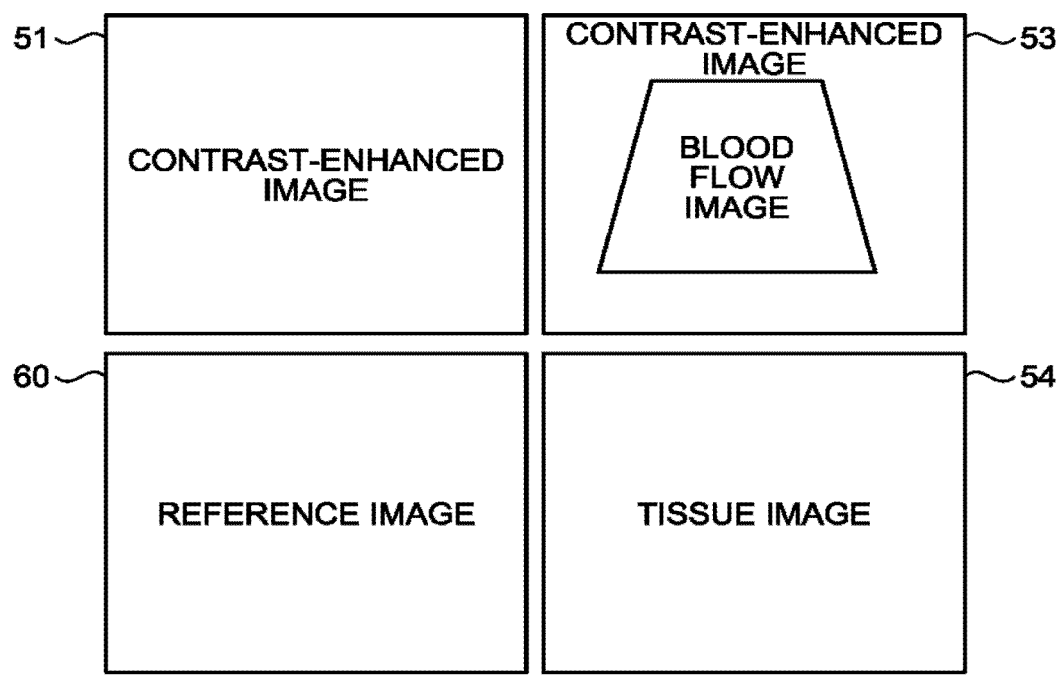
FIG. 23 is a drawing for explaining an example of yet another image display mode according to the fourth modification example of the first embodiment.

In yet another example, as illustrated in FIG. 23, the controlling circuitry 180 may exercise control so that the display 103 displays a reference image 60 in place of the maximum brightness image 56 displayed in the lower left region in FIG. 19. In this situation, the reference image 60 may be a medical image of the subject P acquired by another medical image diagnosis apparatus (e.g., an X-ray Computed Tomography (CT) apparatus or a Magnetic Resonance Imaging (MRI) apparatus) different from the ultrasound diagnosis apparatus. For example, the controlling circuitry 180 causes the display 103 to display, as the reference image 60, a Multi Planar Reconstruction (MPR) image that is generated from volume data by the other medical image diagnosis apparatus while using a so-called fusion function and is taken on the same cross-sectional plane as that of the contrast-enhanced image 51, the blood flow image 52, or the tissue image 54 currently being displayed. The reference image 60 changes in conjunction with changes that are caused by the moving of the ultrasound probe 101 or the like in the contrast-enhanced image 51, the blood flow image 52, or the tissue image 54 currently being displayed.

Further, the reference image 60 may be an image acquired by the ultrasound diagnosis apparatus 1. For example, the reference image 60 may be a blood flow image that is in the same temporal phase as that of the blood flow image 52 currently being displayed and was acquired by the ultrasound diagnosis apparatus 1 during a past medical examination. Similarly, the reference image 60 may be a contrast-enhanced image that is in the same temporal phase as that of the contrast-enhanced image 51 currently being displayed and was acquired by the ultrasound diagnosis apparatus 1 during a past medical examination. Alternatively, the reference image 60 may be a tissue image that is in the same temporal phase as that of the tissue image 54 currently being displayed and was acquired by the ultrasound diagnosis apparatus 1 during a past medical examination.

Further, for example, the reference image 60 may be a blood flow image that is acquired during the same medical examination as that of the blood flow image 52 currently being displayed and is in a different temporal phase from that of the blood flow image 52 currently being displayed. Similarly, the reference image 60 may be a contrast-enhanced image that is acquired during the same medical examination as that of the contrast-enhanced image 51 currently being displayed and is in a different temporal phase from that of the contrast-enhanced image 51 currently being displayed. Further, the reference image 60 may be a tissue image that is acquired during the same medical examination as that of the tissue image 54 currently being displayed and is in a different temporal phase from that of the tissue image 54 currently being displayed. For example, while the display 103 is displaying a contrast-enhanced image 51 in the late phase, the controlling circuitry 180 may cause the display 103 to display a contrast-enhanced image in an arterial phase, as the reference image 60.

Figure 24:
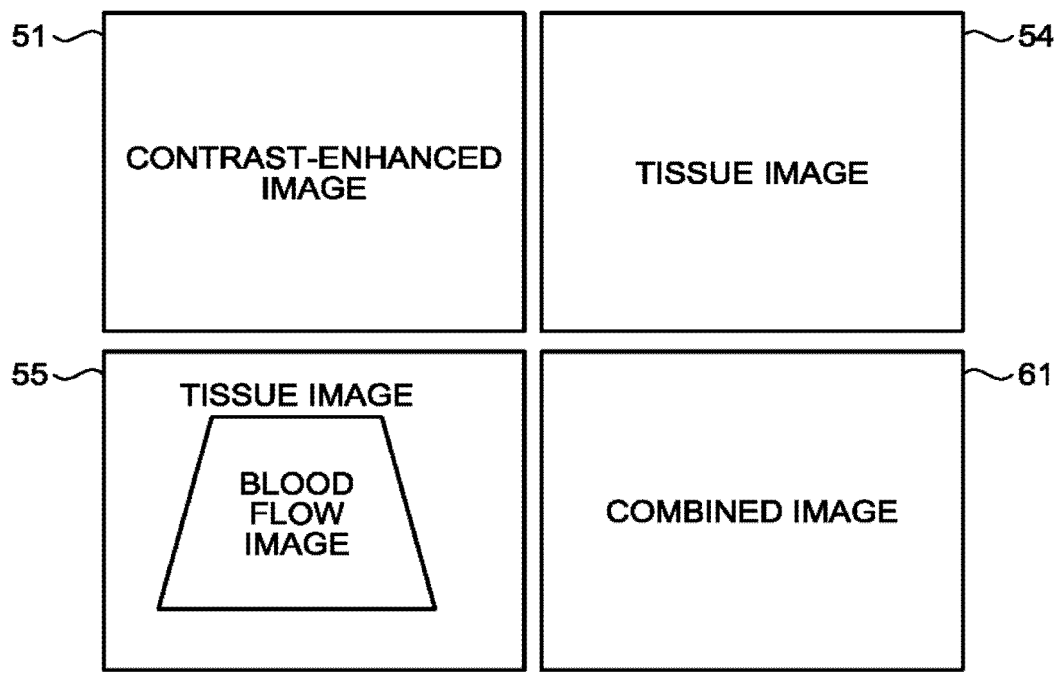
FIG. 24 is a drawing for explaining an example of yet another image display mode according to the fourth modification example of the first embodiment.

In yet another example, as illustrated in FIG. 24, the controlling circuitry 180 may exercise control so that the display 103 displays the contrast-enhanced image 51 in the upper left region, the tissue image 54 in the upper right region, the superimposed image 55 in the lower left region, and a combined image 61 in the lower right region. In this situation, the combined image 61 is an image in which the contrast-enhanced image 51 and the tissue image 54 are combined together and is generated by the image generating circuitry 150. For example, the image generating circuitry 150 generates the combined image 61 by combining together the contrast-enhanced image 51 and the tissue image 54.

Figure 25:
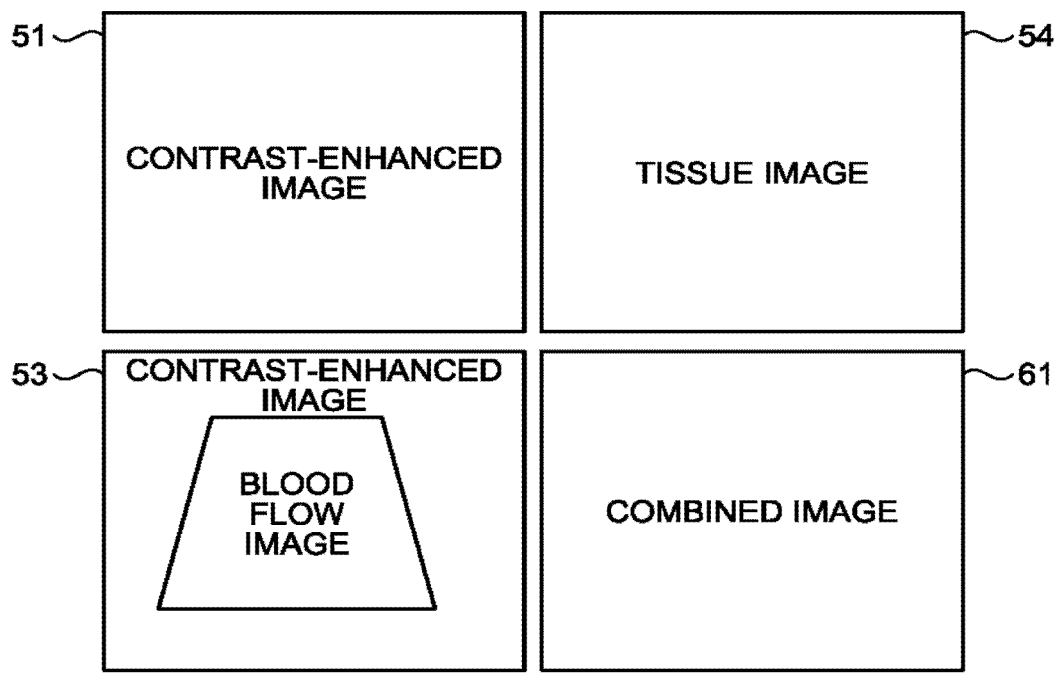
FIG. 25 is a drawing for explaining an example of yet another image display mode according to the fourth modification example of the first embodiment.

In yet another example, as illustrated in FIG. 25, the controlling circuitry 180 may exercise control so that the display 103 displays the superimposed image 53 in place of the superimposed image 55 displayed in the lower left region in FIG. 24.

Figure 26:
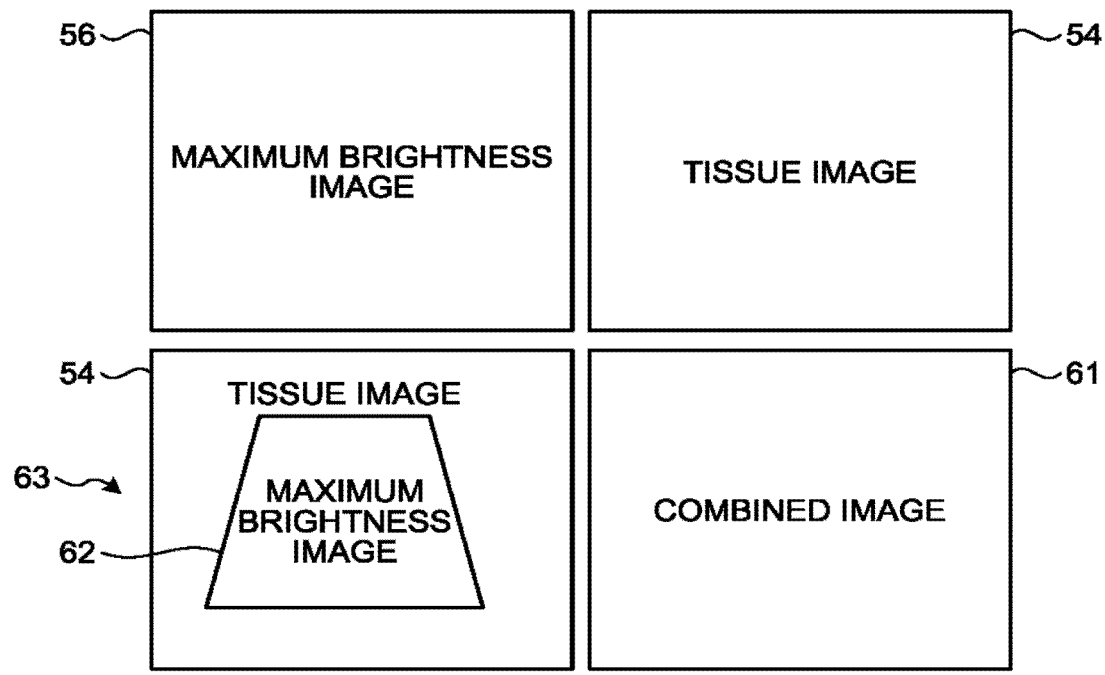
FIG. 26 is a drawing for explaining an example of yet another image display mode according to the fourth modification example of the first embodiment.

In yet another example, as illustrated in FIG. 26, the controlling circuitry 180 may exercise control so that the display 103 displays a superimposed image 63 in which a maximum brightness image 62 is superimposed on the tissue image 54, in place of the superimposed image 55 displayed in the lower left region in FIG. 24.

In this situation, the maximum brightness image 62 and the superimposed image 63 are generated by the image generating circuitry 150. For example, by using the Micro Flow Imaging (MFI) method described above, the image generating circuitry 150 generates the maximum brightness image 62. More specifically, the image generating circuitry 150 performs the maximum brightness retaining calculation on a plurality of blood flow images 52, further selects a maximum brightness level for each of the pixels from among the plurality of blood flow images 52, and generates the maximum brightness image 62 in which each of the pixels is displayed with the selected maximum brightness level. Further, the image generating circuitry 150 generates the superimposed image 63 by superimposing the maximum brightness image 62 on the tissue image 54.

Figure 27:
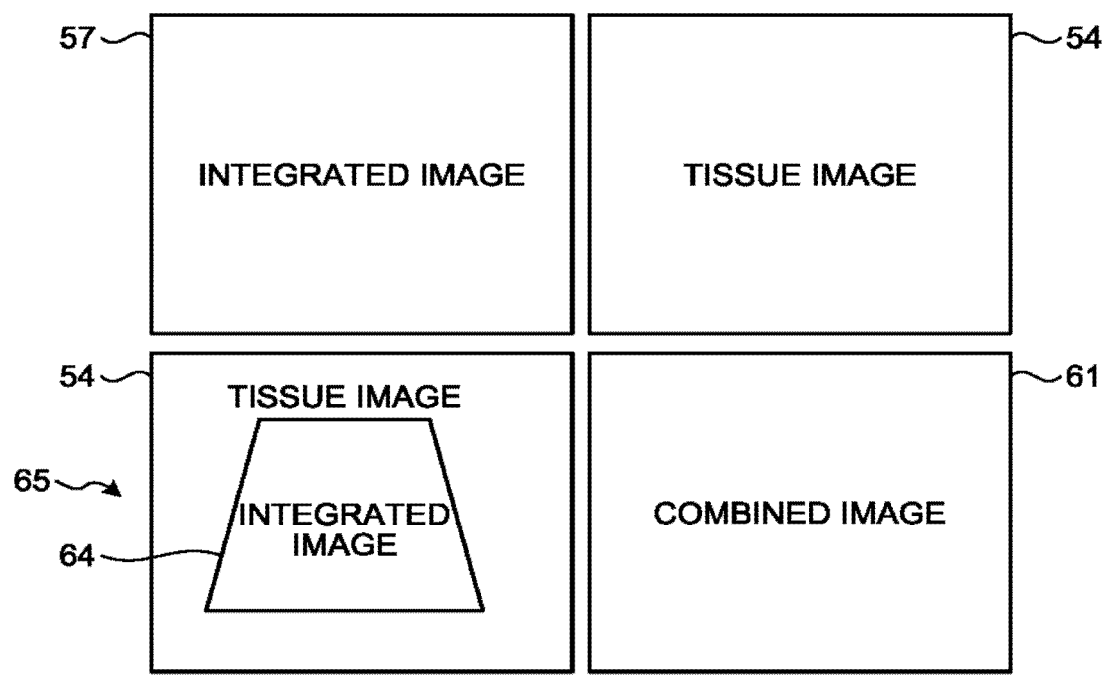
FIG. 27 is a drawing for explaining an example of yet another image display mode according to the fourth modification example of the first embodiment.

In yet another example, as illustrated in FIG. 27, the controlling circuitry 180 may exercise control so that the display 103 displays a superimposed image 65 in which an integrated image 64 is superimposed on the tissue image 54, in place of the superimposed image 55 displayed in the lower left region in FIG. 24. In this situation, the integrated image 64 and the superimposed image 65 are generated by the image generating circuitry 150. For example, the image generating circuitry 150 generates the integrated image 64 by integrating a plurality of blood flow images 52 in a time direction. Further, the image generating circuitry 150 generates the superimposed image 65 by superimposing the integrated image 64 on the tissue image 54.

Figure 28:
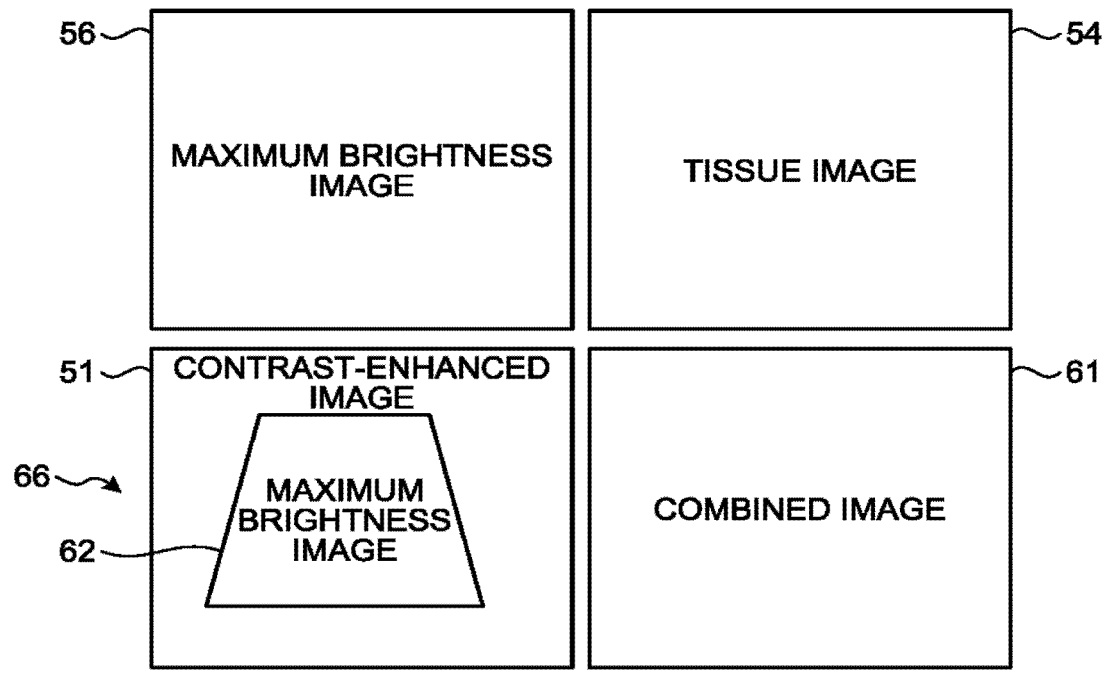
FIG. 28 is a drawing for explaining an example of yet another image display mode according to the fourth modification example of the first embodiment.

In yet another example, as illustrated in FIG. 28, the controlling circuitry 180 may exercise control so that the display 103 displays a superimposed image 66 in which the maximum brightness image 62 is superimposed on the contrast-enhanced image 51, in place of the superimposed image 55 displayed in the lower left region in FIG. 24. In this situation, the superimposed image 66 is generated by the image generating circuitry 150. For example, the image generating circuitry 150 generates the superimposed image 66 by superimposing the maximum brightness image 62 on the contrast-enhanced image 51.

Figure 29:
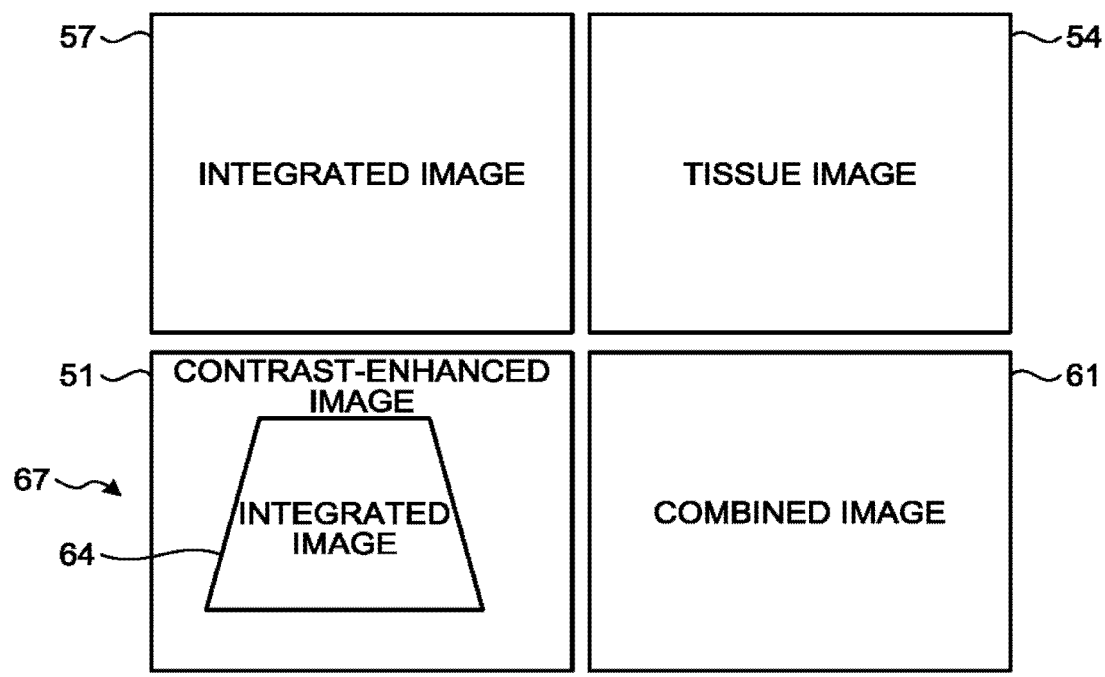
FIG. 29 is a drawing for explaining an example of yet another image display mode according to the fourth modification example of the first embodiment.

In yet another example, as illustrated in FIG. 29, the controlling circuitry 180 may exercise control so that the display 103 displays a superimposed image 67 in which the integrated image 64 is superimposed on the contrast-enhanced image 51, in place of the superimposed image 55 displayed in the lower left region in FIG. 24. In this situation, the superimposed image 67 is generated by the image generating circuitry 150. For example, the image generating circuitry 150 generates the superimposed image 67 by superimposing the integrated image 64 on the contrast-enhanced image 51.

Fifth Modification Example of First Embodiment

In the third modification example of the first embodiment, the example is explained in which the controlling circuitry 180 varies the intervals "T" at which the first ultrasound scans are performed in accordance with the flowrate range. However, the controlling circuitry 180 may vary the intervals "T" in accordance with other conditions. Thus, this modification example will be explained as a fifth modification example of the first embodiment.

In the fifth modification example, for instance, the input device 102 receives priority information from the operator. In this situation, the priority information is, for example, information indicating whether priority is given to increasing the display framerate of the blood flow image 52 to be displayed by the display 103 or to displaying a blood flow image indicating blood flow information about a blood flow having a lower flowrate (e.g., a flowrate equal to or lower than a specific level such as 0.5 cm/s). In this situation, at the stage before the priority information is received by the input device 102, it is assumed that a predetermined initial value is set as the intervals "T" at which the first ultrasound scans are performed.

Further, in accordance with the priority information received by the input device 102, the controlling circuitry 180 changes the intervals "T" at which the first ultrasound scans are performed. For example, an example will be explained in which the priority information indicates that priority is given to increasing the display framerate of the blood flow image 52. In that situation, the controlling circuitry 180 changes the intervals "T" so as to be shorter than the initial value.

Next, an example will be explained in which the priority information indicates that priority is given to displaying a blood flow image indicating blood flow information about a blood flow having a lower flowrate. In that situation, the controlling circuitry 180 changes the intervals "T" so as to be longer than the initial value.

After that, the controlling circuitry 180 controls the transmission circuitry 110a so that the ultrasound probe 101 performs the first ultrasound scans at the post-change intervals "T".

Second Embodiment

In the first embodiment, the first ultrasound scans and the second ultrasound scans are performed so as to alternate. In some situations, however, residual echo of the last ultrasound wave transmitted in a first ultrasound scan may happen to be in the reception time period of the reflected wave of the very first ultrasound wave transmitted in a second ultrasound scan. It is considered that the cause of this problem is that the transmission and reception circuitry 110 transmits the ultrasound wave in the second ultrasound scan, before receiving the reflected-wave from a deep part with respect to the last ultrasound wave transmitted in the first ultrasound scan.

Figure 30A:
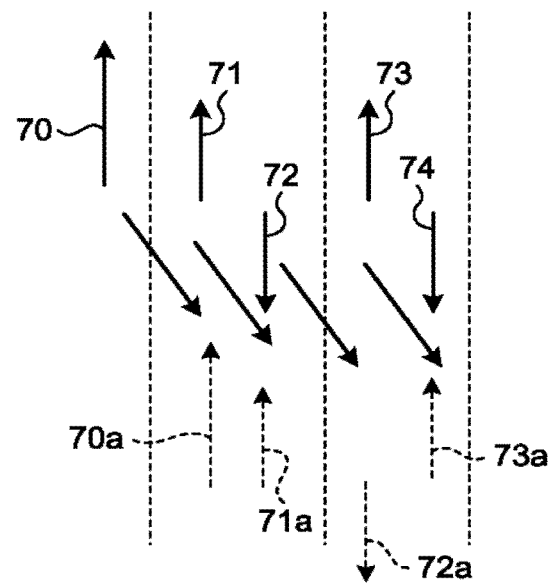
FIG. 30A is a drawing illustrating an example of residual echo.
Figure 30B:
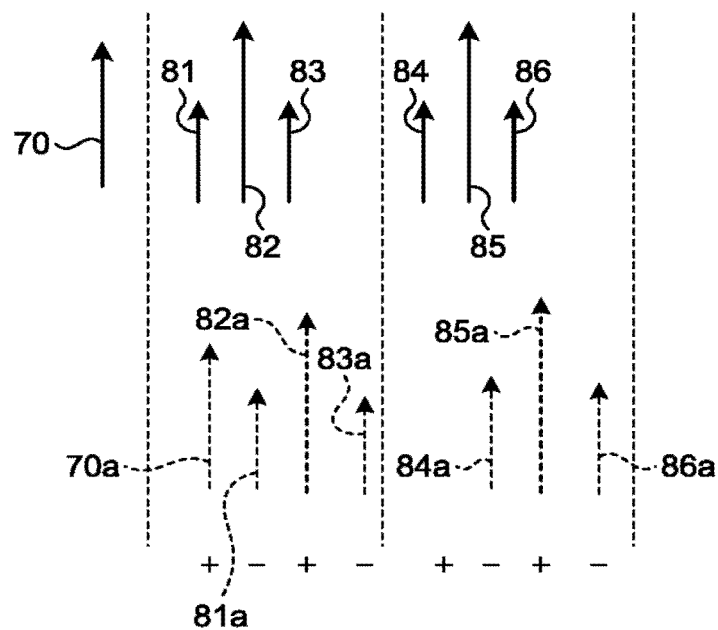
FIG. 30B is a drawing illustrating another example of residual echo.

FIGS. 30A and 30B are drawings illustrating examples of the residual echo. First, an example will be explained in which the phase modulation method is used in the second ultrasound scans. In that situation, as illustrated in FIG. 30A, the transmission and reception circuitry 110 transmits the last ultrasound wave 70 in the first ultrasound scan, and subsequently, transmits two ultrasound waves 71 and 72 having mutually-different phases with respect to the very first scanning line in the second ultrasound scan. After that, the transmission and reception circuitry 110 transmits two ultrasound waves 73 and 74 having mutually-different phases with respect to the second scanning line in the second ultrasound scan.

In this situation, as illustrated in FIG. 30A, residual echo 70a of the ultrasound wave 70 happens to be in the reception time period of the reflected wave of the ultrasound wave 71. Similarly, the respective residual echo 71a to 73a of the ultrasound waves 71 to 73 happen to be in the reception time periods of the respective reflected waves of the ultrasound waves 72 to 74. In this situation, with respect to the second scanning line of the second ultrasound scan, because the residual echo 72a and the residual echo 73a have phases that are different from each other by 180 degrees while the amplitude levels thereof are the same as each other, the residual echo 73a is added to the residual echo 72a, which makes the residual echo equal to "0". However, with respect to the very first scanning line of the second ultrasound scan, because the residual echo 70a and the residual echo 71a have mutually the same phase, while the amplitude levels thereof are not "0", even when the residual echo 71a is added to the residual echo 70a, the residual echo does not become equal to "0".

Next, an example will be explained in which the amplitude modulation method is used in the second ultrasound scans. In that situation, as illustrated in FIG. 30B, the transmission and reception circuitry 110 transmits the last ultrasound wave 70 of the first ultrasound scan, and subsequently, with respect to the very first scanning line of the second ultrasound scan, transmits an ultrasound wave 81 of which the amplitude is "0.5", another ultrasound wave 82 of which the amplitude is "1", and yet another ultrasound wave 83 of which the amplitude is "0.5" in the stated order. After that, with respect to the second scanning line of the second ultrasound scan, the transmission and reception circuitry 110 transmits an ultrasound wave 84 of which the amplitude is "0.5", another ultrasound wave 85 of which the amplitude is "1", and yet another ultrasound wave 86 of which the amplitude is "0.5" in the stated order.

In this situation, as illustrated in FIG. 30B, the residual echo 70a of the ultrasound wave 70 happens to be in the reception time period of the reflected wave of the ultrasound wave 81. Similarly, the respective residual echo 81a, 82a, 84a, and 85a of the ultrasound waves 81, 82, 84 and 85 happen to be in the respective reception time periods of the ultrasound waves 82, 83, 85, and 86. In this situation, with respect to the second scanning line of the second ultrasound scan, because the residual echo 84a, the residual echo 85a, and the residual echo 86a of the ultrasound wave 86 have mutually the same phase, while the amplitude ratio thereof is "1:2:1", when the residual echo 86a is subtracted from residual echo resulting from subtracting the residual echo 84a from the residual echo 85a, the residual echo becomes equal to "0". In contrast, with respect to the very first scanning line of the second ultrasound scan, because the residual echo 70a is present, the residual echo does not become equal to "0".

To cope with this situation, an ultrasound diagnosis apparatus according to the second embodiment configured to provide a countermeasure for such residual echo will be explained. The ultrasound diagnosis apparatus according to the second embodiment further has a function of providing the countermeasure for the residual echo, in addition to the various types of functions of the ultrasound diagnosis apparatus 1 according to the first embodiment.

Figure 31A:
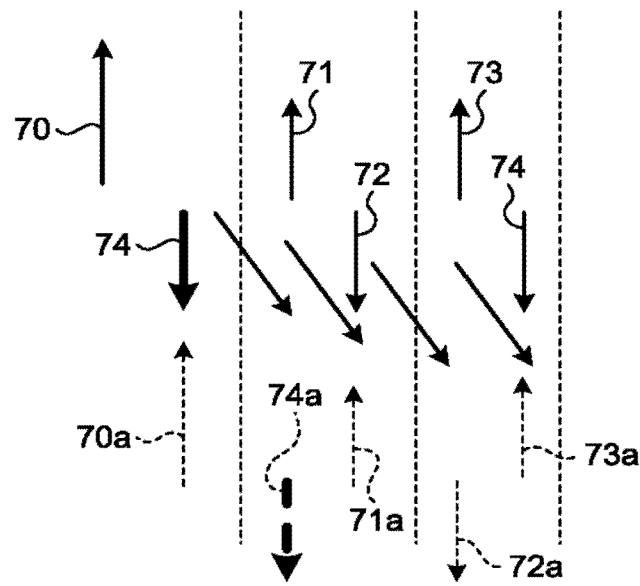
FIG. 31A is a drawing for explaining a countermeasure for residual echo when the phase modulation method is used in the second ultrasound scans.

FIG. 31A is a drawing for explaining the countermeasure for the residual echo in an example in which the phase modulation method is used in the second ultrasound scans. As illustrated in FIG. 31A, the transmission and reception circuitry 110 according to the second embodiment transmits an ultrasound wave 74 that has the same phase and the same amplitude as those of the ultrasound wave 72, as the last ultrasound wave transmitted in the first ultrasound scan. As a result, as illustrated in FIG. 31A, residual echo 74a of the ultrasound wave 74 happens to be in the reception time period of the reflected wave of the ultrasound wave 71. In this situation, with respect to the very first scanning line of the second ultrasound scan, because the residual echo 74a and the residual echo 71a have phases that are different from each other by 180 degrees, while the amplitude levels thereof are the same as each other, the residual echo 71a is added to the residual echo 74a, which makes the residual echo equal to "0". Accordingly, with respect to the very first scanning line of the second ultrasound scan, it is possible to arrange the residual echo equal to be equal to "0".

Figure 31B:
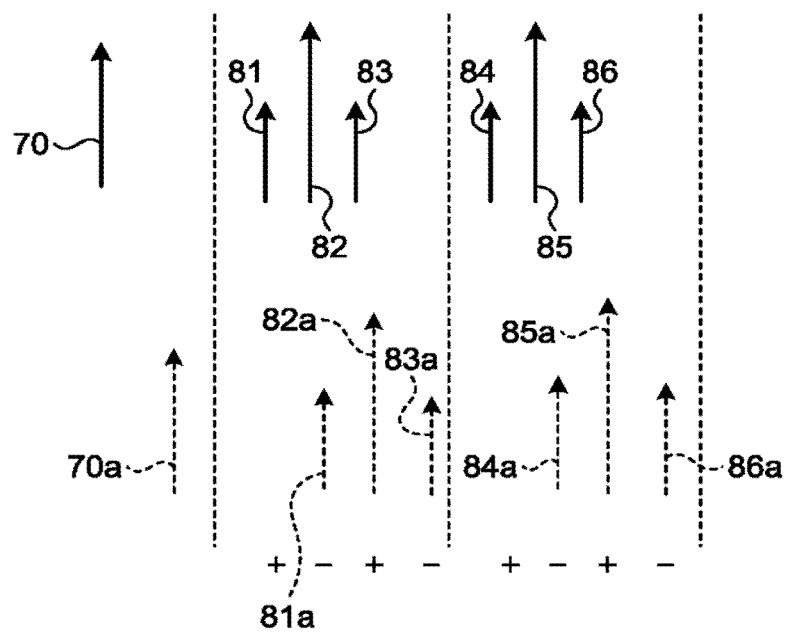
FIG. 31B is a drawing for explaining a countermeasure for residual echo when the amplitude modulation method is used in the second ultrasound scans.

FIG. 31B is a drawing for explaining a countermeasure for the residual echo in an example in which the amplitude modulation method is used in the second ultrasound scans. As illustrated in FIG. 31B, the transmission and reception circuitry 110 according to the second embodiment transmits the very first ultrasound wave 81 of the second ultrasound scan at the time when a predetermined time period has elapsed since the ultrasound wave 70 was transmitted.

In this situation, the predetermined time period is, for example, a time period it takes for each of the ultrasound waves (ultrasound waves 81 to 86) transmitted in the second ultrasound scans to travel a distance 2D that is twice as long as a distance D from the piezoelectric transducer elements of the ultrasound probe 101 to the depth in the contrast-enhanced image 51 based on the second ultrasound scans. In other words, the predetermined time period is a time period corresponding to the depth in the contrast-enhanced image 51.

As a result, as illustrated in FIG. 31B, the residual echo 70a of the ultrasound wave 70 does not come into the reception time period of the reflected wave of the ultrasound wave 81. In this situation, with respect to the very first scanning line of the second ultrasound scan, because the residual echo 81a, the residual echo 82a, and residual echo 83a of the ultrasound wave 83 have mutually the same phase, while the amplitude ratio thereof is "1:2:1", when the residual echo 81a is subtracted from residual echo resulting from subtracting the residual echo 83a from the residual echo 82a, the residual echo becomes equal to "O". Accordingly, with respect to the very first scanning line of the second ultrasound scan, it is possible to arrange the residual echo to be equal to "0".

Figure 32:
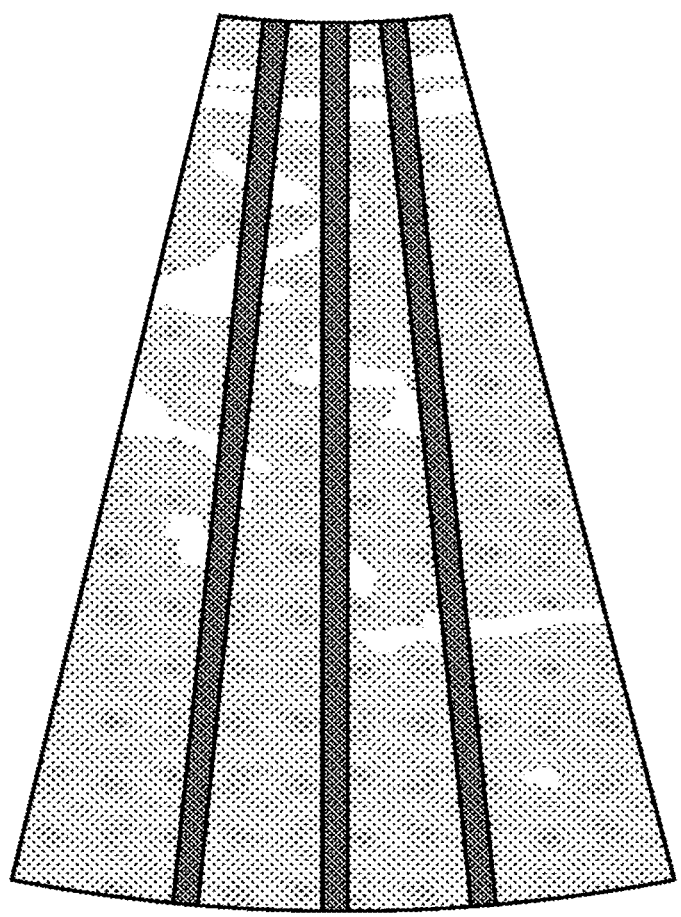
FIG. 32 illustrates an example of a contrast-enhanced image based on the second ultrasound scans illustrated in FIG. 30A or 30B.
Figure 33:
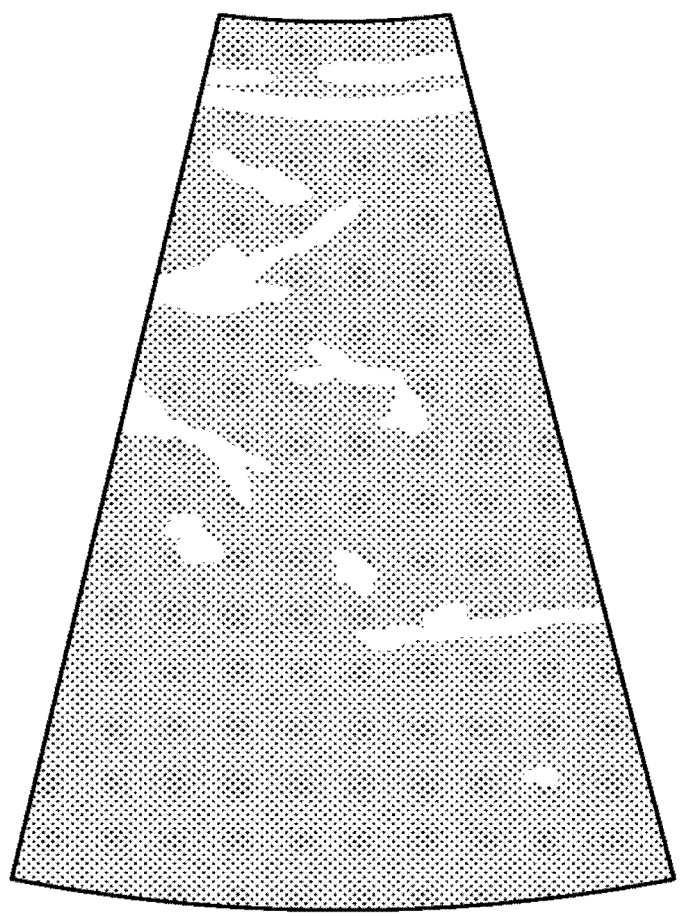
FIG. 33 illustrates an example of a contrast-enhanced image based on the second ultrasound scans illustrated in FIG. 31A or 31B.

FIG. 32 illustrates an example of a contrast-enhanced image based on the second ultrasound scans illustrated in FIG. 30A or 30B. As illustrated in FIG. 32, the residual echo appears in the contrast-enhanced image as a stripe artifact. FIG. 33 illustrates an example of a contrast-enhanced image based on the second ultrasound scans illustrated in FIG. 31A or 31B. In the contrast-enhanced image illustrated in FIG. 33, because the residual echo is equal to "0" in FIG. 31A or 31B, no artifact is caused by the residual echo.

The ultrasound diagnosis apparatus according to the second embodiment has thus been explained. The ultrasound diagnosis apparatus according to the second embodiment is able to provide the countermeasure for the residual echo as explained above. Further, the ultrasound diagnosis apparatus according to the second embodiment is able to acquire, in an excellent manner, at least two selected from among the blood flow image, the contrast-enhanced image, and the tissue image, similarly to the ultrasound diagnosis apparatus 1 according to the first embodiment.

In the embodiments and the modification examples above, the example is explained in which, in the second ultrasound scans, either the phase modulation method or the amplitude modulation method is used. However, in the second ultrasound scans, an amplitude modulation/phase modulation (AMPM) method may be used. The amplitude modulation/phase modulation method is a method by which, for example, two types of ultrasound waves having mutually-different phases and mutually-different amplitude levels are transmitted with respect to each of the scanning lines structuring a scanned range, so as to add together pieces of reflected-wave data based on reflected waves of the two types of ultrasound waves. For example, as examples of the two types of ultrasound waves, the following explanation refers to a first type of ultrasound wave and a second type of ultrasound wave.

For example, the ratio (A1:A2) between the amplitude "A1" of the first type of ultrasound wave and the amplitude "A2" of the second type of ultrasound wave is "1:2". Further, the phase of the first type of ultrasound wave and the phase of the second type of ultrasound wave are different from each other. For example, the phase of the first type of ultrasound wave and the phase of the second type of ultrasound wave are different from each other by 180 degrees.

For example, when the amplitude modulation/phase modulation method is used, the transmission and reception circuitry 110 transmits, with respect to each of the scanning lines structuring each of the segmented regions, three ultrasound waves, namely the first type of ultrasound wave, the second type of ultrasound wave, and the first type of ultrasound wave, in the stated order. After that, the B-mode processing circuitry 130 adds together the pieces of reflected-wave data based on the reflected waves of the three ultrasound waves. When the amplitude modulation/phase modulation method is used, the second ultrasound scans include transmitting and receiving the two types of ultrasound waves having the mutually-different amplitude levels and the mutually-different phases.

Further, in the third modification example above, the example is explained in which the controlling circuitry 180 selects one from between the phase modulation method and the amplitude modulation method in accordance with the flowrate range by using the single threshold value. However, another arrangement is also acceptable in which, in a similar manner, the controlling circuitry 180 selects one from among the phase modulation method, the amplitude modulation method, and the phase modulation/amplitude modulation method, in accordance with the flowrate range, by using two threshold values. In that situation, the controlling circuitry 180 may vary the number of segmented regions into which the second region is to be divided, depending on whether the phase modulation method is selected, the amplitude modulation method is selected, or the amplitude modulation/phase modulation method is selected.

According to at least one aspect of the embodiments and the modification examples explained above, it is possible to acquire, in an excellent manner, at least two selected from among the blood flow image, the contrast-enhanced image, and the tissue image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus for performing an ultrasound scan on a subject who has a contrast agent injected, the ultrasound diagnosis apparatus comprising:
   transmission and reception circuitry configured to perform, via an ultrasound probe, a first ultrasound scan on a first region in the subject and a second ultrasound scan on at least a part of a second region in the subject overlapping with the first region, the second ultrasound scan including transmitting and receiving two types of ultrasound waves of which one or both of amplitude levels and phases are different from each other; and
   processing circuitry configured to generate a blood flow image corresponding to one frame by implementing a Doppler method based on a data sequence including pieces of reception data obtained from the first ultrasound scan performed multiple times in a mutually same position within the first region so as to have the second ultrasound scan performed in-between and to generate a contrast-enhanced image and a tissue image based on a result of the second ultrasound scan performed at least one time, wherein
   the processing circuitry is further configured to
      generate the tissue image corresponding to the second region based on reflected-wave data based on one of the two types of ultrasound waves acquired in the second ultrasound scan on each of a plurality of regions obtained by dividing the second region, and generate the contrast-enhanced image corresponding to the second region based on reflected-wave data based on both of the two types of ultrasound waves acquired in the second ultrasound scan on each of the plurality of regions obtained by dividing the second region.

2. The ultrasound diagnosis apparatus according to claim 1, wherein
the processing circuitry is further configured to obtain the data sequence acquired from the first ultrasound scan performed multiple times with respect to positions in the first region, and further obtain blood flow information by inputting the obtained data sequence to an adaptive Motion Target Indicator (MTI) filter generated based on the data sequence, and
the processing circuitry is further configured to generate the blood flow image based on the blood flow information.

3. The ultrasound diagnosis apparatus according to claim 1, wherein the transmission and reception circuitry is further configured to transmit a very first ultrasound wave of the second ultrasound scan at a time when, since transmission of a last ultrasound wave in the first ultrasound scan at one time, a time period corresponding to a depth in the contrast-enhanced image based on the second ultrasound scan performed subsequent to the first ultrasound scan has elapsed.

4. The ultrasound diagnosis apparatus according to claim 1, wherein the processing circuitry is further configured to cause a display to simultaneously display the blood flow image and the contrast-enhanced image.

5. The ultrasound diagnosis apparatus according to claim 1, wherein the processing circuitry is further configured to cause a display to simultaneously display the blood flow image, the contrast-enhanced image, and the tissue image.

6. The ultrasound diagnosis apparatus according to claim 5, wherein the processing circuitry is further configured to cause the display to display the blood flow image, the contrast-enhanced image, and the tissue image that are arranged along a left-and-right direction.

7. The ultrasound diagnosis apparatus according to claim 5, wherein the processing circuitry is further configured to cause the display to display a superimposed image in which the blood flow image is superimposed on the tissue image, as well as the contrast-enhanced image.

8. The ultrasound diagnosis apparatus according to claim 1, wherein the processing circuitry is further configured to cause storage circuitry to store therein the blood flow image and the contrast-enhanced image independently of each other.

9. The ultrasound diagnosis apparatus according to claim 1, wherein the processing circuitry is further configured to cause storage circuitry to store therein the blood flow image, the contrast-enhanced image, and the tissue image independently of one another.

10. The ultrasound diagnosis apparatus according to claim 4, wherein
the processing circuitry is further configured to generate an integrated image in which a plurality of the contrast-enhanced images or a plurality of the blood flow images are integrated in a time direction, and cause the display to display the integrated image.

11. The ultrasound diagnosis apparatus according to claim 4, wherein
the processing circuitry is further configured to select a maximum brightness level for each pixel from among a plurality of the contrast-enhanced images or a plurality of the blood flow images and generate a maximum brightness image in which each pixel is displayed with the maximum brightness level, and
the processing circuitry is further configured to cause the display to display the maximum brightness image.

12. The ultrasound diagnosis apparatus according to claim 5, wherein the processing circuitry is further configured to generate a combined image by combining together the contrast-enhanced image and the tissue image, and cause the display to display the combined image.

13. The ultrasound diagnosis apparatus according to claim 5, wherein the processing circuitry is further configured to cause the display to display an analysis result image indicating a result of an analysis performed on at least one selected from among the blood flow image, the contrast-enhanced image, and the tissue image.

14. The ultrasound diagnosis apparatus according to claim 5, wherein the processing circuitry is further configured to cause the display to display an aiding image indicating one selected from among: a result of a measuring process related to the subject performed by using at least one of the blood flow image, the contrast-enhanced image, and the tissue image; an operating procedure performed by an operator; and an image quality condition of at least one of the first and the second ultrasound scans.

15. The ultrasound diagnosis apparatus according to claim 5, wherein the processing circuitry is further configured to cause the display to display one selected from among: a reference image of the subject acquired by a medical image diagnosis apparatus other than the ultrasound diagnosis apparatus; and a reference image that is acquired by the ultrasound diagnosis apparatus and of which a temporal phase is different from or same as a temporal phase of the blood flow image, the contrast-enhanced image, or the tissue image currently being displayed.

16. The ultrasound diagnosis apparatus according to claim 1, wherein the transmission and reception circuitry is further configured to perform, via the ultrasound probe, the first ultrasound scan and the second ultrasound scan performed on each of a plurality of segmented regions obtained by dividing the second region, so as to alternate.

17. The ultrasound diagnosis apparatus according to claim 16, wherein
in the second ultrasound scan, the transmission and reception circuitry is further configured to transmit an ultrasound wave by implementing one selected from among a phase modulation method, an amplitude modulation method, and an amplitude modulation/phase modulation method, and
a quantity of the plurality of segmented regions varies depending on whether the transmission and reception circuitry transmits the ultrasound wave by implementing the phase modulation method, by implementing the amplitude modulation method, or by implementing the amplitude modulation/phase modulation method.

18. The ultrasound diagnosis apparatus according to claim 16, wherein the transmission and reception circuitry is further configured to transmit the ultrasound wave based on one selected from among a phase modulation method, an amplitude modulation method, and an amplitude modulation/phase modulation method, in accordance with a flow-rate range.

19. The ultrasound diagnosis apparatus according to claim 2, wherein the transmission and reception circuitry is further configured to perform the first ultrasound scan in which an ultrasound wave is transmitted and received once with respect to each of scanning lines within the first region.

20. The ultrasound diagnosis apparatus according to claim 19, wherein the processing circuitry is further configured to obtain the blood flow information by inputting, to the adaptive MTI filter, the data sequence including the pieces of reception data acquired multiple times in a frame direction by performing the first ultrasound scan multiple times.

21. The ultrasound diagnosis apparatus according to claim 1, wherein the processing circuitry is further configured to change an interval at which the first ultrasound scan is performed in accordance with a flowrate range.

22. The ultrasound diagnosis apparatus according to claim 4, wherein the processing circuitry is further configured to change an interval at which the first ultrasound scan is performed, in accordance with information indicating whether priority is given to increasing a display framerate of the blood flow image to be displayed by the display or to displaying a blood flow image indicating blood flow information about a blood flow having a flowrate equal to or lower than a specific level.

23. The ultrasound diagnosis apparatus according to claim 1, wherein the processing circuitry is further configured to generate the contrast-enhanced image based on the two types of ultrasound waves acquired in the second ultrasound scan, and generate the tissue image based on one type of the two types of ultrasound waves acquired in the second ultrasound scan.

24. The ultrasound diagnosis apparatus according to claim 1, wherein as the blood flow image, the tissue image and the contrast-enhanced image are generated, and the processing circuitry is further configured to update a display of the blood flow image, the tissue image, and the contrast-enhanced image.

25. The ultrasound diagnosis apparatus according to claim 1, wherein the processing circuitry is further configured to cause the blood flow image, the tissue image, and the contrast-enhanced image to be displayed side by side on a display.

26. The ultrasound diagnosis apparatus according to claim 1, wherein the processing circuitry is further configured to cause a first superimposed image in which the blood flow image and the tissue image are superimposed, and a second superimposed image in which the contrast-enhanced image and the tissue image are superimposed to be displayed side by side on a display.

27. The ultrasound diagnosis apparatus according to claim 1, wherein the processing circuitry is further configured to cause a superimposed image in which the blood flow image and the tissue image are superimposed, and the contrast-enhanced image to be displayed side by side on a display.

28. The ultrasound diagnosis apparatus according to claim 1, wherein the processing circuitry is further configured to cause a first superimposed image in which the blood flow image and the tissue image are superimposed, a second superimposed image in which the contrast-enhanced image and the tissue image are superimposed, the contrast-enhanced image and the tissue image to be displayed side by side on a display.

* * * * *